(12) United States Patent      (10) Patent No.:    US 12,612,663 B2

Sussman et al.             (45) Date of Patent:      Apr. 28, 2026

---

(54) MORPHOMETRIC DETECTION OF DNA MISMATCH REPAIR DEFICIENCY

(71) Applicant: VISIONGATE, INC., Phoenix, AZ (US)

(72) Inventors: Daniel J. Sussman, Flagstaff, AZ (US); Michael G. Meyer, Phoenix, AZ (US); Randall Mastrangelo, Gaithersburg, MD (US); Alan C. Nelson, Gig Harbor, WA (US)

(73) Assignee: VisionGate, Inc., Woodinville, WA (US)

( * ) Notice: Subject to any disclaimer, the term of this patent is extended or adjusted under 35 U.S.C. 154(b) by 1169 days.

(21) Appl. No.: 16/972,552

(22) PCT Filed: Jun. 5, 2019

(86) PCT No.: PCT/US2019/035647

§ 371 (c)(1),
(2) Date: Dec. 4, 2020

(87) PCT Pub. No.: WO2019/236743

PCT Pub. Date: Dec. 12, 2019

(65) Prior Publication Data

US 2021/0200987 A1      Jul. 1, 2021

Related U.S. Application Data

(60) Provisional application No. 62/681,593, filed on Jun. 6, 2018.

(51) Int. Cl.

| | |
|---|---|
| *G01N 33/48* | (2006.01) |
| *C12Q 1/6886* | (2018.01) |
| *G01N 15/14* | (2006.01) |
| *G06F 18/214* | (2023.01) |
| *G06N 20/00* | (2019.01) |
| *G06T 7/00* | (2017.01) |
| *G06V 20/69* | (2022.01) |
| *G01N 15/01* | (2024.01) |

(52) U.S. Cl.

CPC ....... *C12Q 1/6886* (2013.01); *G01N 15/1468* (2013.01); *G06F 18/214* (2023.01); *G06N 20/00* (2019.01); *G06T 7/0012* (2013.01); *G06V 20/698* (2022.01); *C12Q 2600/112* (2013.01); *C12Q 2600/156* (2013.01); *G01N 15/01* (2024.01); *G06T 2207/10056* (2013.01); *G06T 2207/10072* (2013.01); *G06T 2207/20081* (2013.01); *G06T 2207/30024* (2013.01); *G06V 2201/03* (2022.01)

(58) Field of Classification Search

None

See application file for complete search history.

(56) References Cited

U.S. PATENT DOCUMENTS

| | | |
|---|---|---|
| 6,522,775 B2 | 2/2003 | Nelson |
| 7,738,945 B2 | 6/2010 | Fauver et al. |
| 7,835,561 B2 | 11/2010 | Meyer et al. |
| 7,907,765 B2 | 3/2011 | Fauver et al. |
| 8,155,420 B2 | 4/2012 | Meyer et al. |
| 8,254,023 B2 | 8/2012 | Watson et al. |
| 2016/0157786 A1 | 6/2016 | Gupta |
| 2017/0003267 A1 | 1/2017 | Meyer et al. |
| 2017/0140124 A1 | 5/2017 | Sehgal et al. |

OTHER PUBLICATIONS

Hejna, Miroslav, et al. "High accuracy label-free classification of single-cell kinetic states from holographic cytometry of human melanoma cells." Scientific reports 7.1 (2017): 11943.*

Choi, Wonshik, et al. "Tomographic phase microscopy." Nature methods 4.9 (2007): 717-719.*

Neumann, Thomas, et al. "Simultaneous 3D imaging of morphology and nanoparticle distribution in single cells with the Cell-CT™ technology." 2008 30th Annual International Conference of the IEEE Engineering in Medicine and Biology Society. IEEE, 2008.*

Nandakumar, Vivek, et al. "Isotropic 3D nuclear morphometry of normal, fibrocystic and malignant breast epithelial cells reveals new structural alterations." PloS one 7.1 (2012): e29230.*

Abdel-Wahab et al., "Chapter 8: Adverse Events in Cancer Immunotherapy," in *Immunotherapy, Advances in Experimental Medicine and Biology 995*, eds. Naing et al., 2017, pp. 155-174.

Alexander et al., "Histopathological Identification of Colon Cancer with Microsatellite Instability," *American Journal of Pathology* 158(2):527-535, 2001.

Bai et al., "Interaction between Human Mismatch Repair Recognition Proteins and Checkpoint sensor Rad9-Rad1-Hus1," *DNA Repair (Amst)* 9(5):478-487, 2010. (23 pages).

Bailis et al., "An Inducible, Isogenic Cancer Cell Line System for Targeting the State of Mismatch Repair Deficiency," *PLoS One* 8(10):e78726, 2013. (11 pages).

Böcking et al., "Diagnosis of Bronchial Carcinoma on Sections of Paraffin-Embedded Sputum—Sensitivity and Specificity of an Alternative to Routine Cytology," *Acta Cytologica* 36(1):37-47, 1992.

Bornens, "Cell Polarity: Intrinsic or Externally Imposed?" *The New Biologist* 3(6):627-636, 1991.

Borghaei et al., "Nivolumab verses Docetaxel in Advanced Nonsquamous Non-Small-Cell Lung Cancer," *The New England Journal of Medicine* 373:1627-1639, 2015.

(Continued)

*Primary Examiner* — Anna Skibinsky

(74) *Attorney, Agent, or Firm* — Seed Intellectual Property Law Group LLP

(57) ABSTRACT

A method to develop one or more morphometric classifiers to identify a mismatch repair deficiency (MMRD). The method provides a non-invasive method of characterizing MMRD that is responsive to a tumor in its early stages of development and irrespective of the tumor size. The method allows targeting cancer therapy to the specific characteristics of the cancer that the patient may have, allowing more efficient cancer management with far fewer side effects.

4 Claims, 9 Drawing Sheets

(56) References Cited

OTHER PUBLICATIONS

Boussiotis, "Somatic Mutations and Immunotherapy Outcome with CTLA-4 Blockade in Melanoma," *N Engl J Med* 371(23):2230-2232, 2014. (5 pages).

Breiman, "Random Forests," *Machine Learning* 45:5-32, 2001.

Byun et al., "Cancer immunotherapy-immune checkpoint blockade and associated endocrinopathies," *Nat Rev Endocrinol* 13(4):195-207, 2017. (30 pages).

Carbognin et al., "Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers," *PloS ONE* 10(6): e0130142, 2015.

Carbone et al., "First-Line Nivolumab in Stave IV or Recurrent Non-Small-Cell Lung Cancer," *The New England Journal of Medicine* 376(25):2415-2426, 2017.

Chae et al., "Concordance of Genomic Alterations by Next-Generation Sequencing in Tumor Tissue versus Circulating Tumor DNA in Breast Cancer," *Molecular Cancer Therapeutics* 16(7):1412-1420, 2017.

Danilova et al., "Association of PD-1/PD-L axis expression with cytolytic activity, mutational load, and prognosis in melanoma and other solid tumors," *PNAS*: E7769-E7777, 2016.

Davis et al., "Is Circulating Tumor DNA (Ctdna) Use Ready for Prime Time? Applications and Challenges of Ctdna in the Era of Precision Oncology," *Chemo Open Access* 6(2): 1000230, 2017. (2 pages).

Deans, *The Radon Transform and Some of Its Applications*, Dover Publications, Inc., Mineola, New York, 2007, 308 pages.

Debes et al., "p300 Modulates Nuclear Morphology in Prostate Cancer," *Cancer Res.* 65(3):708-712, 2005.

Di Muzio et al., "Maximum intensity projection," retrieved from Radiopaedia.org, https://doi.org/10.53347/rID-14801, 2011. (4 pages).

Fauver et al., "Three-dimensional imaging of single isolated cell nuclei using optical projection tomography," *Optics Express* 13(11):4210, 2005. (14 pages).

Gangadhar et al., "Mitigating the toxic effects of anticancer immunotherapy," *Nature Reviews Clinical Oncology* 11:91-99, 2014.

Gisselsson et al., "Abnormal Nuclear Shape in Solid Tumors Reflects Mitotic Instability," *American Journal of Pathology* 158(1):199-206, 2001.

Goodman et al., "Tumor Mutational Burden as an Independent Predictor of Response to Immunotherapy in Diverse Cancers," *Molecular Cancer Therapies* 16(11):2598-2608, 2017.

Greenson et al., "Phenotype of Microsatellite Unstable Colorectal Carcinomas," *The American Journal of Surgical Pathology* 27(5):563-570, 2003.

Hodi et al., "Improved Survival with Ipilimumab in Patients with Metastatic Melanoma," *The New England Journal of Medicine* 363:711-723, 2010.

Ionov et al., "A role for p300/CREB binding protein genes in promoting cancer progression in colon cancer cell lines with microsatellite instability," *PNAS* 101(5):1273-1278, 2004.

Iwabuchi et al., "Three-dimensional Reconstruction and Fractal Geometric Analysis of Serrated Adenoma," *Jpn. J. Cancer Res.* 93:259-266, 2002.

Kefford et al., "Clinical Efficacy and correlation with tumor PD-L1 expression in patients (pts) with melanoma (MEL) treated with the anti-PD-1 monoclonal antibody MK-3475," *Journal of Clinical Oncology* 32(15 Suppl):3005, 2014.

Kim et al., "Clinical and Pathological Characteristics of Sporadic Colorectal Carcinomas with DNA Replication Errors in Microsatellite Sequences," *American Journal of Pathology* 145(1): 148-156, 1994.

Korbar et al., "Deep Learning for Classification of Colorectal Polyps on Whole-slide Images," *Journal of Pathology Informatics* 1:30, 2017. (9 pages).

Koshiishi et al., "p300 gene alterations in intestinal and diffuse types of gastric carcinoma," *Gastric Cancer* 7:85-90, 2004.

Le et al., "Mismatch-repair deficiency predicts response of solid tumors to PD-1 blockade," *Science* 357(6349):409-413, 2017. (15 pages).

Madore et al., "PD-L1 expression in melanoma shows marked heterogeneity within and between patients: implications for anti-PD-1/PD-L1 clinical trials," *Pigment Cell Melanoma Res.* 28:248-253, 2014.

Mattout et al., "Chromatin states and nuclear organization in development - a view from the nuclear lamina," *Genome Biology*, 2015, 15 pages.

Meads et al., "Polarity and Nucleation of Microtubules in Polarized Epithelial Cells," *Cell Motility and the Cytoskeleton* 32:273-288, 1995.

Meyer et al., "The Cell-CT 3-Dimensional Cell Imaging Technology Platform Enables the Detection of Lung Cancer Using the Noninvasive LuCED Sputum Test," *Cancer Cytopathology* 123:512-523, 2015.

Mitchell et al., "ORAL13.06 PDL-1 Expression in NSCLC: Analysis of a Large Early Stage Cohort; and Concordance of Expression in Primary, Nodes and Metastasis," *Journal of Thoracic Oncology* 10(9, Supplement 2):S199, 2015.

Motzer et al., "Nivolumab verses Everolimus in Advanced Renal-Cell Carcinoma," *The New England Journal of Medicine* 373:1803-1813, 2015.

Muro et al., "Relationship between PD-L1 expression and clinical outcomes in patients (Pts) with advanced gastric cancer treated with the anti-PD-1 monoclonal antibody pembrolizumab (Pembro; MK-3475) in KEYNOTE-012," *Journal of Clinical Oncology* 33(3, Supplement):3, 2015.

Nelson et al., "Morphometric Genotyping Identifies Lung Cancer Cells Harboring Target Mutations; Cell-CT® Platform Detects Gene Abnormalities," *Journal of Thoracic Oncology* 12(11S2):S2278-S2279, Abstract No. P3.03-016, 2017.

Neumann et al., "Premalignant and Malignant Cells in Sputum From Lung Cancer Patients," *Cancer Cytopathology* 117:473-481, 2009.

Pardoll, "The blockade of immune checkpoints in cancer immunotherapy," *Nature Reviews Cancer* 12:252-264, 2012.

Pihan et al., "Centrosome Defects Can Account for Cellular and Genetic Changes That Characterize Prostate Cancer Progression," *Cancer Research* 61:2212-2219, 2001.

Polak et al., "Cell-or-origin chromatin organization shapes the mutational landscape of cancer," *Nature* 518:360-364, 2015.

Reddy et al., "Higher order chromatin organization in cancer," *Semin Cancer Biol.* 23(2):109-115, 2013. (14 pages).

Rizvi et al., "Mutational landscape determines sensitivity to PD-1 blockade in non-small cell lung cancer," *Science* 348(6230):124-128, 2015. (12 pages).

Rizzolo et al., "Apical Orientation of the Microtubule Organizing Center and Associated γ-Tubulin during the Polarization of the Retinal Pigment Epithelium in Vivo," *Developmental Biology* 157:147-156, 1993.

Robert et al., "Nivolumab in Previously Untreated Melanoma without *BRAF* Mutation," *The New England Journal of Medicine* 372(4):320-330, 2015.

Robinson et al., "DNA Mismatch Repair and Chk1-Dependent Centrosome Amplification in Response to DNA Alkylation Damage," *Cell Cycle* 6(8):982-992, 2007.

Schapire et al., *Boosting—Foundations and Algorithms*, The MIT Press, Cambridge, Massachusetts, London, England, 2012, 528 pages.

Schreiber et al., "Performance Characteristics of Different Modalities for Diagnosis of Suspected Lung Cancer," *Chest* 123:115S-128S, 2003.

Schuster-Böckler et al., "Chromatin organization is a major influence on regional mutation rates in human cancer cells," *Nature* 488:504-507, 2012.

Viale et al., "Mismatch Repair Deficiency as a Predictive Biomarker for Immunotherapy Efficacy," *Hindawi BioMed Research International* 2017:Article ID 4719194, 2017, 7 pages.

Voong et al., "Beyond PD-L1 testing-emerging biomarkers for immunotherapy in non-small cell lung cancer," *Ann Transl Med* 5(18):376, 2017. (14 pages).

(56) References Cited

OTHER PUBLICATIONS

Ward et al., "Microsatellite instability and the clinicopathological features of sporadic colorectal cancer," *Gut* 48:821-829, 2001.

Weber et al., "Nivolumab versus chemotherapy in patients with advanced melanoma who progressed after anti-CTLA-4 treatment (CheckMate 037): a randomized, controlled, open-label, phase 3 trial," *Lancet Oncol* 16:375-384, 2015.

Whitehead et al., "Regulation and Regulatory Activities of Centrosomes," *Journal of Cellular Biochemistry Supplements* 32/33:192-199, 1999.

Wilbur et al., "Automated 3-Dimensional Morphologic Analysis of Sputum Specimens for Lung Cancer Detection: Performance Characteristics Support Use in Lung Cancer Screening," *Cancer Cytopathology* 123:548-556, 2015.

Zink et al., "Nuclear Structure in Cancer Cells," *Nature Reviews Cancer* 4:677-687, 2004.

* cited by examiner

FIG. 3A    FIG. 3B    FIG. 3C

5 Microns

Normal Ciliated Columnar Cell

Individual Cilia Strand

Figure 7:
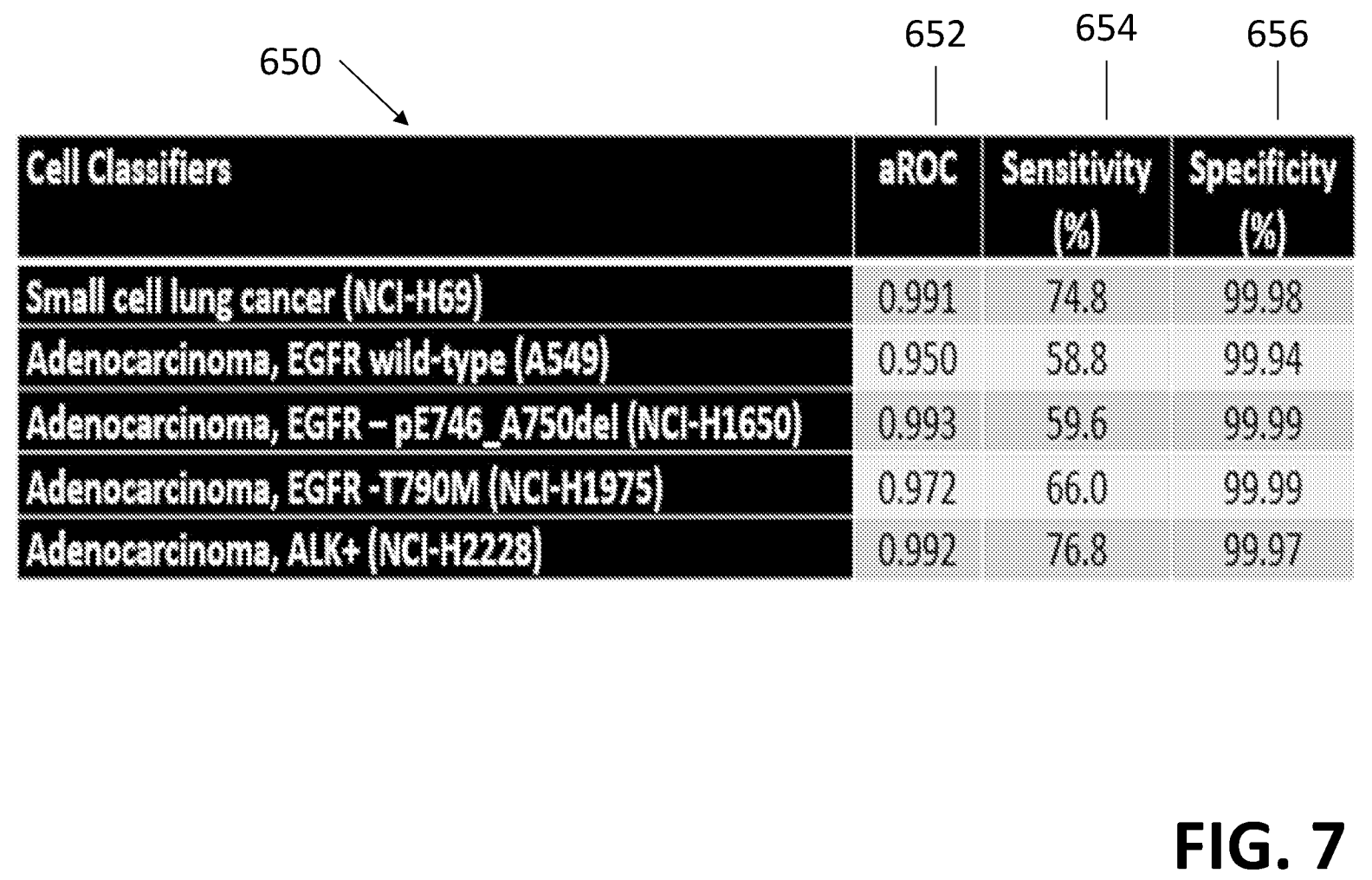

| Cell Classifiers | aROC | Sensitivity (%) | Specificity (%) |
|---|---|---|---|
| Small cell lung cancer (NCI-H69) | 0.991 | 74.8 | 99.98 |
| Adenocarcinoma, EGFR wild-type (A549) | 0.950 | 58.8 | 99.94 |
| Adenocarcinoma, EGFR – pE746_A750del (NCI-H1650) | 0.993 | 59.6 | 99.99 |
| Adenocarcinoma, EGFR -T790M (NCI-H1975) | 0.972 | 66.0 | 99.99 |
| Adenocarcinoma, ALK+ (NCI-H2228) | 0.992 | 76.8 | 99.97 |

MORPHOMETRIC DETECTION OF DNA MISMATCH REPAIR DEFICIENCY

TECHNICAL FIELD

The present invention relates to optical tomography on a cellular and sub-cellular scale. More particularly, the invention relates to a system and method for developing one or more morphometric classifiers to identify DNA mismatch repair deficiency (MMRD).

BACKGROUND

Lung cancer is the second most prevalent cancer in the United States and is the most lethal. Over 31 million patients in the United States (US) are at high risk for the development of lung cancer, primarily due to age, smoking history, and pollution and other factors including radon exposure, family history of lung cancer, etc. Approximately 160,000 US patients die of lung cancer each year. At the time of this writing, lung cancer can only be cured with surgery when detected in early stages, mainly stage I and II. However, lung cancer is known to be preceded by pre-cancerous conditions presenting as dysplastic cells. The detection of such pre-cancerous conditions can trigger preventative treatment that can reduce the risk of contracting lung cancer.

Alterations in nuclear morphology have been a major histopathological biomarker for cancer detection for the last 140 years. The direct link between the chromatin organization in the cell nucleus and cell function at the DNA replication, translation and protein expression level has been demonstrated in a number of published studies[1-3]. In particular, chromatin organization which underlies nuclear 3D architecture has been implicated as a major factor influencing regional and global mutation rates in human cancers cells[4,5]

A current approach to treating a variety of cancers involves targeting the immune system checkpoint inhibitors CTLA4, PD-1, and PD-L1, proteins that are involved in allowing tumors to evade the immune system response.[6] While durable responses have been achieved using immunotherapy on numerous solid tumors, only a subset of patients truly benefit. For example, the following are response rates to single-agent PD-1/PD-L1 inhibition: 40% for melanoma,[7,8] 25% for non-small cell lung cancer (NSCLC),[9,10] and 19% for renal cell carcinoma.[11] In addition, current immunotherapies harbor strong risks for adverse side effects[12-14]. As a result, robust biomarkers that can reliably predict which patients will benefit from immunotherapeutic treatment are needed to reduce the unnecessary burden of inflammatory and immune-related adverse effects on the patient.

Several biomarkers have been identified that assist in predicting patient response to immunotherapy.[15] One such biomarker is the expression of PD-L1, which is necessary for therapeutic response, but not sufficient for determining response due to tumor heterogeneity and measurement of expression levels.[16-21] More recently it has been discovered that mismatch repair (MMR) deficiency and tumor mutational burden (TMB; the number of somatic, coding, base substitution, and indel mutations per megabase of genomic DNA) are good predictors of response to immunotherapy.[15, 22-27] MMR deficiency (MMRD) lead to genomic and microsatellite instability (MSI) and high TMB resulting in the expression of neoantigens, which makes tumor cells more susceptible to attack by cytotoxic T cells.[23] Challenges in detecting MMRD either from solid tumors or ctDNA include the inability to biopsy, sensitivity in detection in early stage disease, and lack of concordance in data obtained using paired tissue and different NGS (next generation sequencing) platforms.[28, 29] A more rapid, minimally invasive, and less expensive approach, as described below using the VisionGate Cell-CTT technology, is to detect MMRD in cancer cells based on its potential to confer morphometric changes to structural biomarkers which can be quantified optically in 3D at sub-micron spatial scale. The demonstrated link between chromatin organization and genomic DNA mutation rates suggests the existence of structural biomarkers in the cell nucleus that could be used to detect genomic instability and/or more specific types of genomic alterations in cancer.

The ability to detect MMRD through measurement of structural biomarkers is supported by a number of studies. Studies have reported on histopathological differences in colorectal carcinomas with defects in MMR resulting in microsatellite mutations. In general, these tumors were mucinous and poorly differentiated, consisting of cells that were relatively large, round, and regular with abundant amphophilic cytoplasm.[30-32] In addition, Alexander et al.[33] reported that colon cancers with MSI exhibited signet ring cells and cribriforming. A study by Gisselsson et al.[34] found that abnormalities in nuclear shape is an indicator of genetic instability in short-term tumor cell cultures. In cultures from 58 tumors of bone, soft tissue, and epithelium, nuclear blebs, strings, and micronuclei were significantly more frequent in tumors that contained genetic instability. Other cell culture systems that have revealed a link between DNA repair and nuclear morphology include the following studies. Bai et al.[35] reported that alkylating agent treatment of Hela cells in which Rad9 expression has been knocked down results in abnormal nuclear morphology. Debes et al.[36] showed that transfection of p300 into prostate cancer cells in culture induces quantifiable nuclear alterations, such as diameter, perimeter, and absorbance. The p300 gene and the highly homologous CREB binding protein (CBP) gene together are mutated in >85% of microsatellite instability (MSI)+ colon cancer cell lines[37] and the loss of heterozygosity at the p300 locus was observed in advanced intestinal-type gastric cancer.[38]

Another structural biomarker that is linked to tumor progression is the centrosome. Defects in MMR and genomic instability are closely linked to the increased numbers of structurally abnormal centrosomes.[39, 40] Centrosomes play a crucial role in many microtubule-mediated processes, such as establishing cell shape and cell polarity.[41-44]

As described above, morphological changes based on defects in MMR and MSI have been implicated in multiple types of cancers. While the data presented below establishes the ability of the Cell-CT™ platform to perform morphometric genotyping on lung adenocarcinoma cell lines with different driver mutations, the utility of this technology should be applicable to identifying MMR deficiency and mutational burden in a variety of cancers.

In related developments, advances in 3D imaging of biological cells using optical tomography have been deployed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-Projection Formation for Optical Tomography,"

(Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein, an early lung cancer detection technology has been developed by VisionGate, Inc., Phoenix, AZ to provide measurement advantages that have demonstrated a great improvement in the operating characteristics of conventional morphologic cytology analyses.

Processing in such an optical tomography system begins with specimen collection and preparation. For diagnostic applications in lung disease, patient specimens can be collected non-invasively in a clinic or at home. At the clinical lab, the specimen is processed to remove non-diagnostic material, fixed and then stained. Stained specimens are then mixed with an optical gel, and the suspension is injected into a microcapillary tube. Images of objects, such as cells, in the specimen are collected while the cells are rotated around 360-degrees relative to the image collection optics in an optical tomography system. The resultant images comprise a set of extended depth of field images from differing perspectives called "pseudo-projection images." The set of pseudo-projection images can be mathematically reconstructed using backprojection and filtering techniques to yield a 3D reconstruction of a cell of interest. Having isometric or roughly equal resolution in all three dimensions is an advantage in 3D tomographic cell imaging, especially for quantitative feature measurements and image analysis. Building on the teachings therein an early lung cancer detection technology has been developed by VisionGate, Inc., Phoenix, Ariz. to provide measurement advantages that have the potential to greatly improve the operating characteristics of conventional morphologic cytology analyses. Published clinical data[45,46] shows that non-invasive sputum analysis using the Cell-CT™ platform detects early stage lung cancer with high sensitivity (92%) and specificity (95%).

The 3D reconstructed digital image then remains available for analysis in order to enable the quantification through the measurement of sub-cellular structures, molecules or molecular probes of interest. An object such as a biological cell may be stained or labeled with at least one absorbing contrast agent or tagged molecular probe, and the measured amount and structure of this biomarker may yield important information about the disease state of the cell, including, but not limited to, various cancers such as lung, breast, prostate, cervical, stomach, esophageal, pancreatic cancers and various stages of dysplasia.

However, until the disclosure herein, there was no reliable method for employing optical tomography for classifying the presence of MMRD. By providing here a method and system for identifying the presence of MMRD in targeted cells, a patient with early stage cancer may benefit being treated with an immune checkpoint inhibitor agent in order to improve outcome. The identification of the presence of MMRD in premalignant cells found in biological fluids such as sputum may also serve as a biomarker for therapeutic efficacy, such as the use of iloprost.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is a method for developing one or more morphometric classifiers to identify cells exhibiting MMRD. Selected clones are derived from transduced cells and the selected clones are analyzed for MLH1 expression to screen for those with levels that have been substantially reduced in comparison to a parental cell line. The selected clones are expanded in culture and harvested. The MMRD level is determined, then the selected clones are analyzed on a 3D microscopy optical tomography system; and the selected clones are compared to a set of control transduced cell lines.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 7 tabulates results of an experimental study in a table that indicates the area under the ROC (aROC) and sensitivity and specificity for a target cell.

Figure 1:
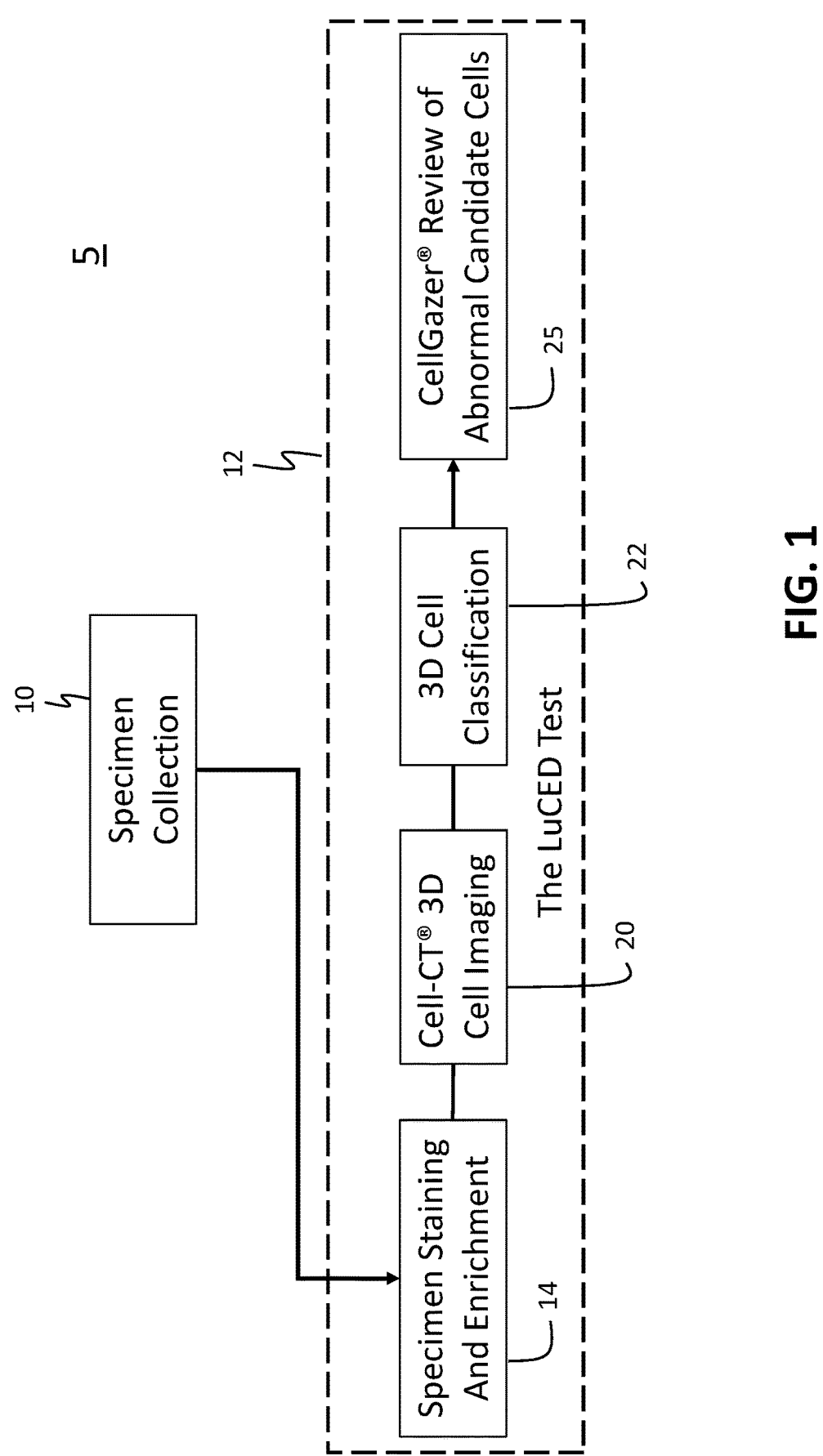
FIG. 1 schematically shows a functional overview of a lung cancer test for analysis of a specimen.

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements and have been solely selected for ease of recognition in the drawings.

DETAILED DESCRIPTION OF THE
PREFERRED EMBODIMENTS

The following disclosure describes a method of developing one or more morphometric classifiers to identify MMRD expression. Several features of methods and systems in accordance with example embodiments are set forth and described in the figures. It will be appreciated that methods and systems in accordance with other example embodiments can include additional procedures or features different than those shown in the figures. Example embodiments are described herein with respect to an optical tomography cell imaging system. However, it will be understood that these examples are for the purpose of illustrating the principles, and that the invention is not so limited.

Definitions

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one example," "an example" or combinations and/or variations of these terms means that a particular feature, structure or characteristic described in connection with the embodiment is included in at least one embodiment of the present disclosure. Thus, the appearances of the phrases "in one embodiment" or "in an example" in various places throughout this specification are not necessarily all referring to the same example and/or embodiment. Furthermore, the particular features, structures, or characteristics may be combined in any suitable manner in one or more examples and/or embodiments.

"Adequacy" refers to the content of the specimen and defines a limit for target cells to determine if a sufficient cellular pellet has been analyzed.

"Calcitriol" as used herein is a synthetic (man-made) active form of vitamin D3 (cholecalciferol).

"Capillary tube" has its generally accepted meaning and is intended to include transparent microcapillary tubes and equivalent items with an inside diameter generally of 500 microns or less, but larger diameters could be used.

"Cell" means biological cell such as a human, mammal or animal cell.

The "Cell-CTT platform" refers to an optical tomography system manufactured by VisionGate, Inc. of Phoenix, AZ incorporating teachings of the Nelson and Fauver patents referenced herein above and improvements of those teachings. The Cell-CT™ platform is an automated, high-resolution 3D tomographic microscope and computing system for imaging cells in flow. The Cell-CT™ platform computes 3D cell images with equal spatial resolution in all dimensions (isotropic resolution) allowing measurements to be independent of orientation, as opposed to the conventional optical imaging methods. Further, eliminating the focal plane ambiguity and view orientation dependencies typical of conventional microscopy provides information content to automatically recognize a broad spectrum of cell types, and unambiguously identify rare abnormal cells in a predominantly normal cell population.

"CellGazer" a software-based utility being developed to foster review of 2D and 3D images of cells rendered by the Cell-CT. The result of cell review is a detailed differential diagnosis of the cell type that then determines the final result of a case processed, for example by the LuCED test.

"Chimeric antigen receptors (CARs)" as used herein mean Artificial T cell receptors (also known as chimeric T cell receptors, or chimeric immunoreceptors) are engineered receptors, which graft an arbitrary specificity onto an immune effector cell.

"CIS" as used herein has its generally accepted meaning of Carcinoma in situ, also known as in situ neoplasm.

"Depth of field" is the length along the optical axis within which the focal plane may be shifted before an unacceptable image blur for a specified feature is produced.

"Enrichment" refers to the process of extracting target cells from a raw specimen. The process yields an enriched sample whose cells can then be more efficiently imaged on the Cell-CT system.

"Immunotherapy" as used herein applies to the field of oncology and means a method of ameliorating, treating, or preventing a malignancy in a human subject wherein the steps of the method assist or boost the immune system in eradicating cancerous cells, including the administration of cells, antibodies, proteins, or nucleic acids that invoke an active (or achieve a passive) immune response to destroy cancerous cells. It also encompasses the co-administration of biological adjuvants (e.g., interleukins, cytokines, *Bacillus* Comette-Guerin, monophosphoryl lipid A, etc.) in combination with conventional therapies for treating cancer such as chemotherapy, radiation, or surgery, administering any vaccine that works by activating the immune system to prevent or destroy cancer cell growth and in vivo, ex vivo, and adoptive immunotherapies, including those using autologous and/or heterologous cells or immortalized cell lines.

"Iloprost" as used herein is an immunomodulating agent which comprises a synthetic analogue of prostacyclin $PGI_2$.

"LuCED® test" refers to an early lung cancer detection test employing the Cell-CT® platform as developed by VisionGate, Inc. of Phoenix, AZ incorporating the teachings of the Nelson and Fauver patents referenced hereinabove and improvements of those teachings.

"The LuCED® process" refers to the mechanism of 3D cell reconstruction, classification to find abnormal cells, and pathology confirmation.

"Object" means an individual cell, human cell, mammal cell, item, thing or other entity.

"Pseudo-projection" includes a single image representing a sampled volume of extent larger than the native depth of field of the optics where pseudo-projection images thus formed include an integration of a range of focal plane images from a fixed viewpoint. The concept of a pseudo-projection is taught in Fauver '945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"ROC" has its generally accepted meaning of Receiver Operator Characteristic.

"Sample" means a finished cellular preparation that is ready for analysis, including all or part of an aliquot or specimen.

"Subject" as used herein means a human patient.

"Target Cell" refers to a cell from a specimen whose characterization or enumeration is especially desired. For example, in the LuCED test, the target cells are the normal bronchial epithelial cells. A minimum number of these must be enumerated during the test in order for a specimen to be considered as adequate.

"Threshold" as used in the context of image processing includes a decision boundary value for any measurable characteristic of a feature. Thresholds may be predetermined or set according to instrument specifications, acceptable error rates, statistics, or other criteria according to accepted pattern recognition principles.

"Tumor Mutational Burden" (TMB) means the number of somatic, coding, base substitution, and indel mutations per megabase of genomic DNA.

"TNM stage" is used herein in its generally accepted sense within the context of lung cancer and means tumor, node, metastasis (TNM) staging as defined by medical associations as, for example, by The International Association for the Study of Lung Cancer (IASLC).

Vorinostat also known as suberanilohydroxamic acid is used in its usual meaning as a histone de-acetylace (HDAC) inhibitor used in Barrett's esophagus.

"Voxel" as used in the context of image processing is a volume element on a 3D grid.

Overview

Referring to FIG. 1, a functional overview of a lung dysplasia and cancer test system for analysis of a specimen is schematically shown. The test system 5 includes apparatus and methods for specimen collection 10 followed by a test for early lung cancer detection 12 such as, for example, the LuCED® test. The early lung cancer test 12 further includes an apparatus and methods for specimen staining and enrichment 14, 3D cell imaging 20, 3D cell classification 22 and clinician review of abnormal candidate cells 25.

If sputum is used, collection is typically done through spontaneous coughs in the patient's home or through induction in a clinic. Other types of specimen collection, such as, for example, a biopsy, may be done under clinical conditions. The sample is processed to remove contaminants and non-bronchial epithelial cells as, for example, by de-bulking the white cells and oral squamous cells. The enriched specimen is processed on the Cell-CTT platform that images cells digitally in true 3D with isometric, sub-micron resolution as disclosed, for example in Nelson and Fauver referenced above. The bio-signatures associated with cancer are measured on the 3D cell images and combined into a score that is used to identify those few cells that have cancer characteristics. These cells are then optionally displayed for manual cytologist review using a review station such as a CellGazer™ review station as developed by VisionGate, Inc., Phoenix, AZ. The review station provides visual displays allowing a cytologist to view cell images in 2D and 3D to establish a definitive normal or abnormal status for specific cell candidates. Three-dimensional (3D) cell classification 22 may be carried out using techniques as disclosed herein below.

The cell imaging system 20 includes a process implemented through computer software executed, for example, by a personal computer interfacing with opto-mechanical devices to correct for motion arising during image capture. Most cell images emerge from filtered back-projection in a well-reconstructed way. Cells that were poorly reconstructed are rejected from further processing. One example of a method for detecting poor quality reconstructions is taught by Meyer et al. in U.S. Pat. No. 8,155,420, issued Apr. 10, 2012 and entitled "System and Method for Detecting Poor Quality in 3D Reconstructions," the disclosure of which is incorporated herein by reference.

Earlier attempts at the development of a lung cancer-screening program were based on sputum cytology which showed an insufficient sensitivity to disease detection by human eye (about 60% on average) but with very good specificity (Schreiber and McCrory (2003) Chest 123 (1 Supplement): 115). This experience led some to conclude that sputum is not valuable for detection of lung cancer. A careful analysis involving sputum embedded in paraffin blocks (Böcking A, Biesterfeld S, Chatelain R, Gien-Gerlach G, Esser E., Diagnosis of bronchial carcinoma on sections of paraffin-embedded sputum. Sensitivity and specificity of an alternative to routine cytology. Acta Cytol. 1992; 36(1):37-47) showed that the specimen actually contains abnormal cells in 86% or more of cancer patients. Collection by morning coughs over three successive days yielded optimal results. A further analysis showed that abnormal cells are present in sputum stratified by all relevant clinical factors, including tumor histologic type, size, stage and location (Neumann T, Meyer M, Patten F, Johnson F, Erozan Y, Frable J, et al. Premalignant and Malignant Cells in Sputum from Lung Cancer Patients. Cancer Cytopathology, 2009; 117(6):473-481.). Based on these specimen characteristics, the presently disclosed lung cancer detection test employs spontaneous cough sputum. Initial evaluations have shown satisfactory results using sputum fixation by either Cytoyt (Hologic, Marlborough, MA) or the well-known Saccomanno's method. The question of specimen adequacy is also important for sputum cytology. Attempts at increasing the volume of the sputum expectorate have met with varied success. Sputum induction increases production of phlegm to help achieve an overall adequate sample.

Examples of Sample Enrichment and Preparation

In one example of a lung cancer detection test adapted for detection of dysplasia, specimens undergo three stages of processing prior to analysis: 1) cell isolation and cryopreservation; 2) enrichment by fluorescence activated cell sorting (FACS); and 3) embedding of enriched cells into optical oil that is index-matched to the optical components of the optical tomography imaging system.

Cryopreservation and FACS Enrichment (FACS being One Example)

Sputum is treated with the mucolytic agent dithiothreitol (DTT) (Fisher Scientific, Waltham, MA). In one example, for longer term storage, the specimen was filtered through a 41 μm nylon net and kept at −80° C. in 15% dimethyl sulfoxide (DMSO) (Fisher Scientific, Waltham, MA). After filtration, an aliquot of up to 100 μL of the preserved specimen is removed for lung cancer detection test analysis. First, sputum cells were stained with hematoxylin (Electron Microscopy Sciences, Hatfield, PA) for downstream lung cancer detection test imaging. Cells were then treated with an antibody cocktail containing fluorescent conjugates chosen to both enrich for bronchial epithelial cells and to deplete contaminating inflammatory cells (neutrophils and macrophages). An anticytokeratin-FITC conjugate cocktail (Cell Signaling, Danvers, MA) targets cytokeratins expressed in both normal and malignant epithelial cells. An Anti-CD45-APC conjugate (Mylteni, Bergisch Gladbach, Germany) targets inflammatory cells for negative selection. Cells are also stained with DAPI (Life Technologies, Grand Island, NY) prior to cell sorting. For FACS enrichment, a DAPI-positive mother gate was created to exclude doublet cells and debris, followed by exclusion of high side-scatter events, which are primarily oral squamous cells. Subsequently, a cytokeratin-high (High FITC) and CD45-Low (Low APC) daughter gate is drawn. The population of cells in this daughter gate were the enriched target epithelial cells sorted for a more efficient and downstream lung cancer detection test analysis using an optical tomography system such as the Cell-CT™ optical tomography system.

Embedding of Enriched Cells

Following FACS enrichment (or any other process of enrichment), cells are dehydrated in ethanol followed by suspension in xylene. The cells are then transferred to and embedded in a suitable volume of the optical medium. The optical medium is a viscous oil with matching refractive index for the optical tomography system. Once embedded, cells are injected into a disposable cartridge for imaging on the optical tomography system.

Figure 2:
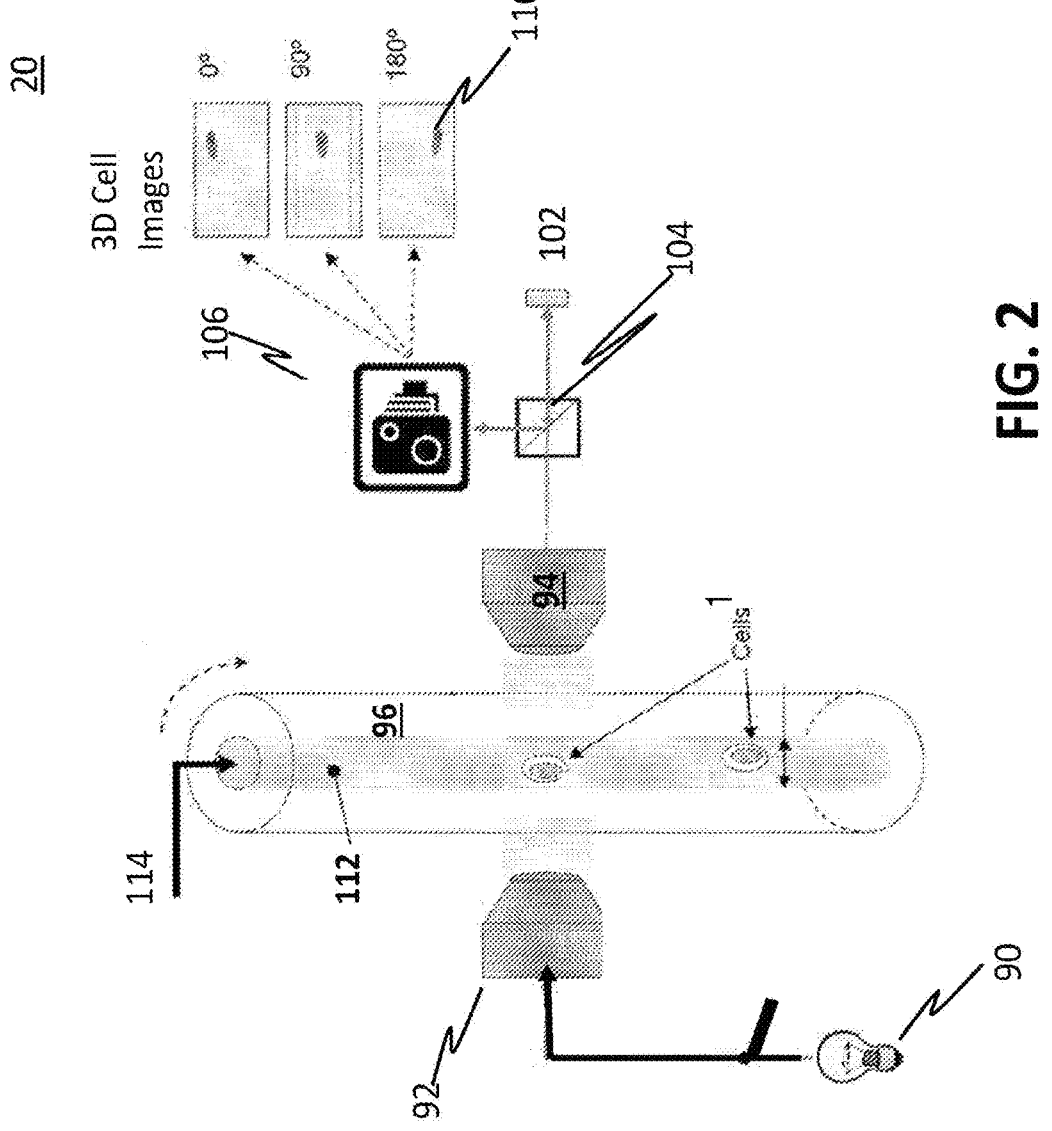
FIG. 2 schematically shows basic system components of a 3D optical tomography imaging system used in a lung cancer test system.

Referring now to FIG. 2, basic system components of a 3D optical tomography imaging system used in a lung cancer test system. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high-speed camera produces a plurality of pseudo-projection images 110. A set of pseudo-projection images for numerous axial tube rotation positions is produced for each object.

Although the test system is not limited to any one contrast method, in one example the lung cancer detection test specifically targets cell morphology based on the traditionally used hematoxylin stain. In the lung cancer detection test application, the optical tomography system computes 3D cell images with equal resolution in all dimensions (i.e. isotropic resolution) allowing measurements to be independent of orientation. Further, eliminating the focal plane ambiguity and view orientation dependencies typical of conventional microscopy provides information content to automatically recognize a broad spectrum of cell types, and unambiguously identify rare abnormal cells in a predominantly normal cell population. The optical tomography system output identifies about 0.5% of all cells as abnormal candidates to be verified using the CellGazer™ (VisionGate, Phoenix, AZ) workstation, an imaging software tool that allows human review of images free of focal plane and orientation ambiguity.

Optical tomography system imaging is performed on a small-volume liquid suspension. For lung cancer detection testing these cells are from the enriched epithelial cell population noted above. Because the optical tomography system can separate closely coincident objects, a narrowly focused core of single file cell flow, although a requirement in standard flow cytometry, is unnecessary.

The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, "Optical Tomography System with High-Speed Scanner," which is also incorporated herein by reference. In operation, stained nuclei of a biological cell 1 are suspended in an optical media 112 and injected into a capillary tube 96 having, for example, a 62 μm inner diameter. The capillary system has been designed to be disposable, thus eliminating the possibility of cross-contamination between specimens. Pressure 114 is applied to the fluid moves objects 1 into position for imaging, before 3D data is collected as the tube rotates. A mirror 102 is actuated to sweep the plane of focus through the object, and the image is integrated by the camera to create a pseudo-projection from each single perspective. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses.

A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell may be rotated to allow capture of a set of 500 pseudo-projections is taken as the capillary rotates through 360 degrees. Because the cells are suspended in a fluid medium, they are prone to a small amount of movement while pseudo-projection images 110 are collected.

Cell images in the pseudo-projections, therefore, must be registered to a common center so that the cell features reinforce one another during the reconstruction. U.S. Pat. No. 7,835,561, entitled "Method for Image Processing and Reconstruction of Images for Optical Tomography," discloses error correction techniques for pseudo-projections. U.S. Pat. No. 7,835,561 is hereby incorporated by reference. The set of corrected pseudo-projections is processed using a filtered back-projection algorithm, similar to that in use in conventional X-ray CT, to compute the tomographic 3D cell reconstruction. Pseudo-projections images 110 taken at three angular positions: 0 g, 90 g and 180 g are shown. Illumination is provided by a light source 90 at 585 nm wavelength to optimize image contrast based on the hematoxylin absorption spectrum. In the reconstruction, 3D pixels or voxels are cubic, with a size of 70 nm in each dimension. Reconstruction volumes vary in size, as the image collection volume is cropped around the object. Typically, volumes are approximately 200-300 pixels on the side.

Figure 3:
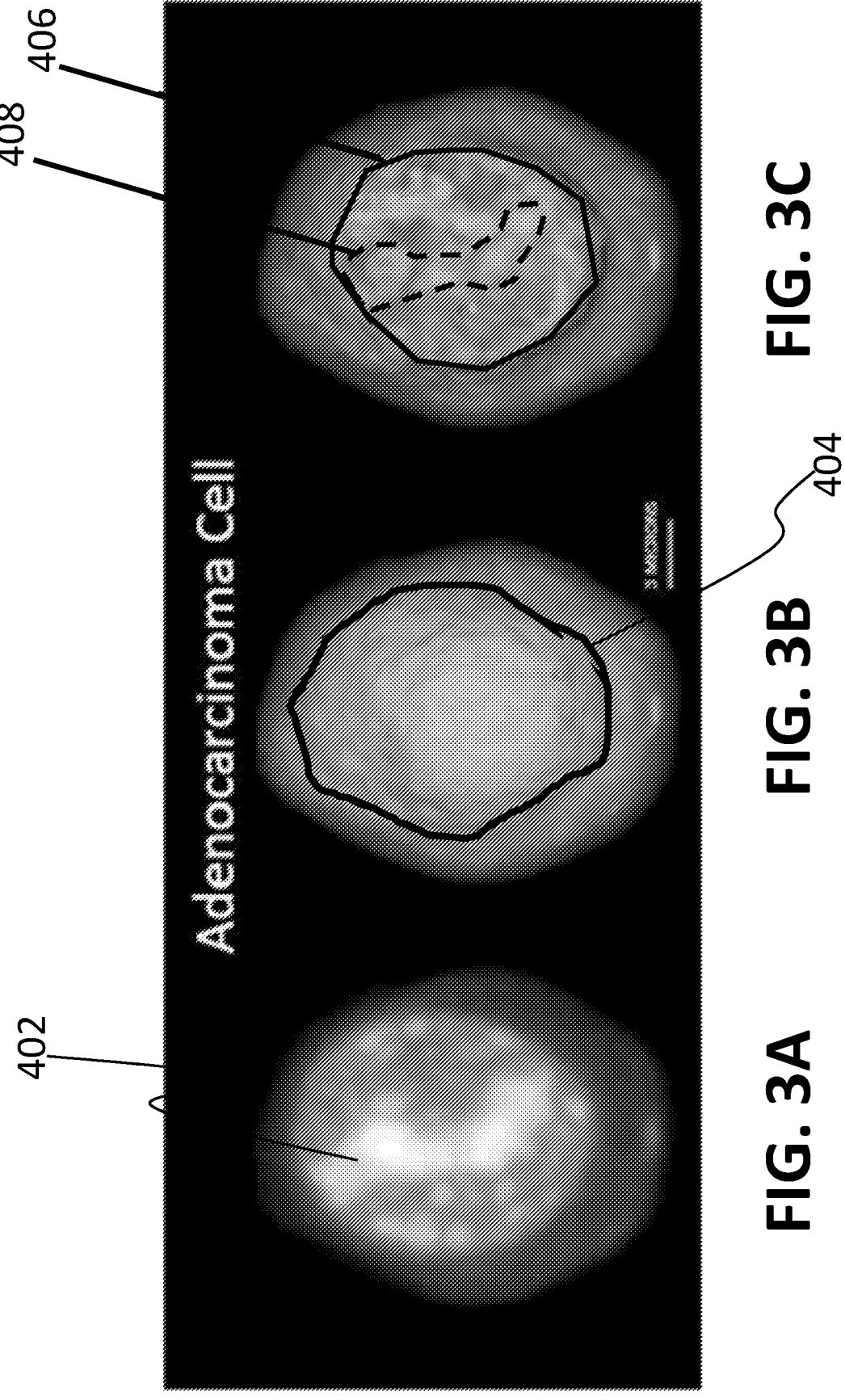
FIG. 3A-FIG. 3C show single perspective views of a 3D image of an adenocarcinoma cell.

Referring now to FIG. 3A-FIG. 3C perspective views of a 3D image of an adenocarcinoma cell are shown. FIG. 3A shows the adenocarcinoma cell in maximum intensity projection[13]. Since grey values in the 3D image are associated with various cell features a look-up table that maps cell structures to color and opacity values was established to produce the cell image at center (as shown in FIG. 3B) and right (as shown in FIG. 3C). In color reproductions of these images, the cytoplasm is represented in translucent white 402, the nucleus in opaque blue 404, the loose chromatin and nucleoplasm in translucent green 406 and the condensed chromatin, and nucleoli are represented in opaque red 408. Given the strictures on international patent regulations to provide only black and white drawings these colors have been identified by borders identified by the corresponding reference numbers 404, 406 and 408 (shown as a broken line border).

Figure 4:
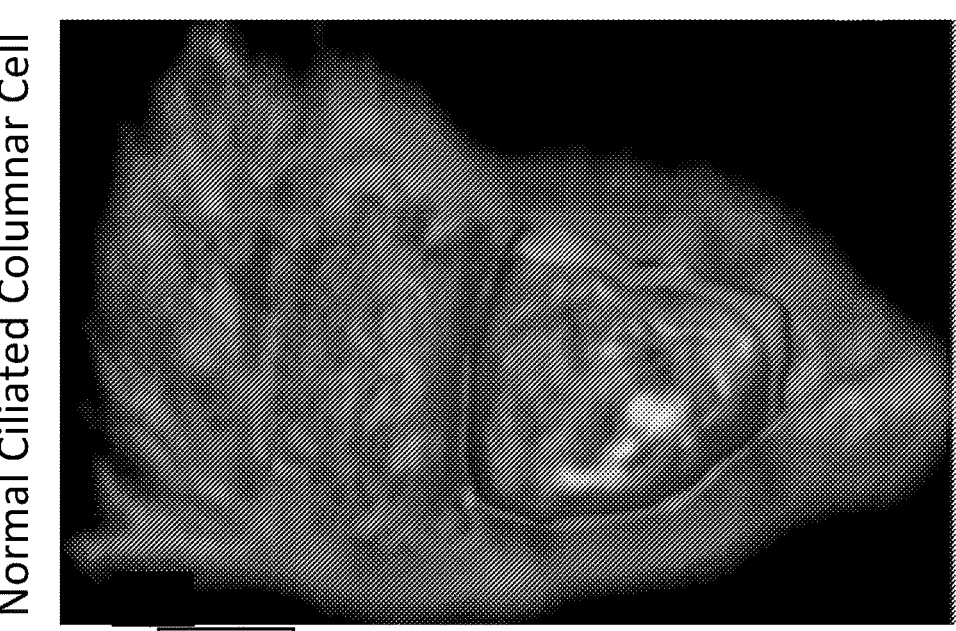
FIG. 4 shows cilia on lung columnar cell.

Referring now to FIG. 4, cilia on a lung columnar cell are shown. An imaged normal bronchial epithelial cell showing individual cilia strands measuring about 250 nm in diameter. This further demonstrates the resolution of the 3D cell imaging system.

Figure 5:
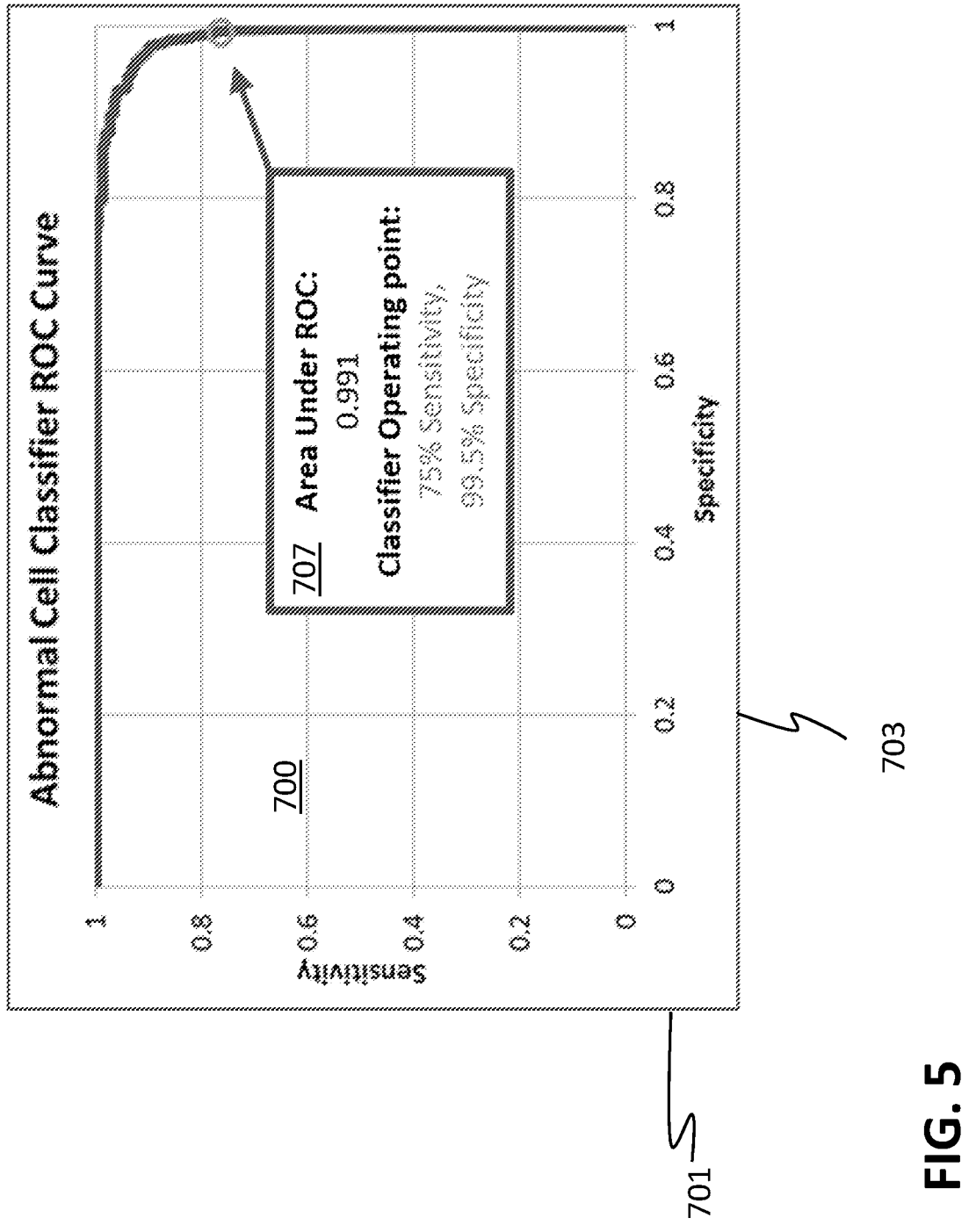
FIG. 5 shows an ROC curve of sensitivity vs. specificity for an abnormal cell classifier.

Referring now to FIG. 5, an ROC curve for an abnormal cell classifier. ROC curve 700 is a plot of sensitivity to dysplastic cells on the vertical axis 701 against specificity on the horizontal axis 703 is shown. Point 707 indicates a region where the dysplastic cell classifier performs with 75% sensitivity at nearly 100% specificity. The classifier was constructed using a data set including cells indicating an abnormal lung process consisting of moderate to severe dysplasia and some atypical cellular conditions. Training of the classifier was implemented using a set of about 150 known dysplastic cells and about 25,000 known normal cells. Accuracy is demonstrated by the single cell ROC curve 700 which shows near perfect detection of dysplastic cells. Classifier accuracy is often expressed as the area under the ROC curve (aROC). Perfect discrimination results when the aROC is 1. The LuCED™ aROC value is 0.991. For single cell detection, an operating point was selected that provides 75% sensitivity and 100% specificity. Cell classification relates to detection of the case as shown in the list below. For example, if one abnormal cell was encountered during LuCED™ analysis then the case detection probability would be 0.75, or 75%. If two abnormal cells were encountered by LuCED™ analysis then the case detection probability would be $(1-(1-0.75)^2)=0.9375$ or nearly 94% case sensitivity, etc.

1 cell—75% case sensitivity, 2 cells—94% case sensitivity, and 3 cells—98% case sensitivity.

Figure 6:
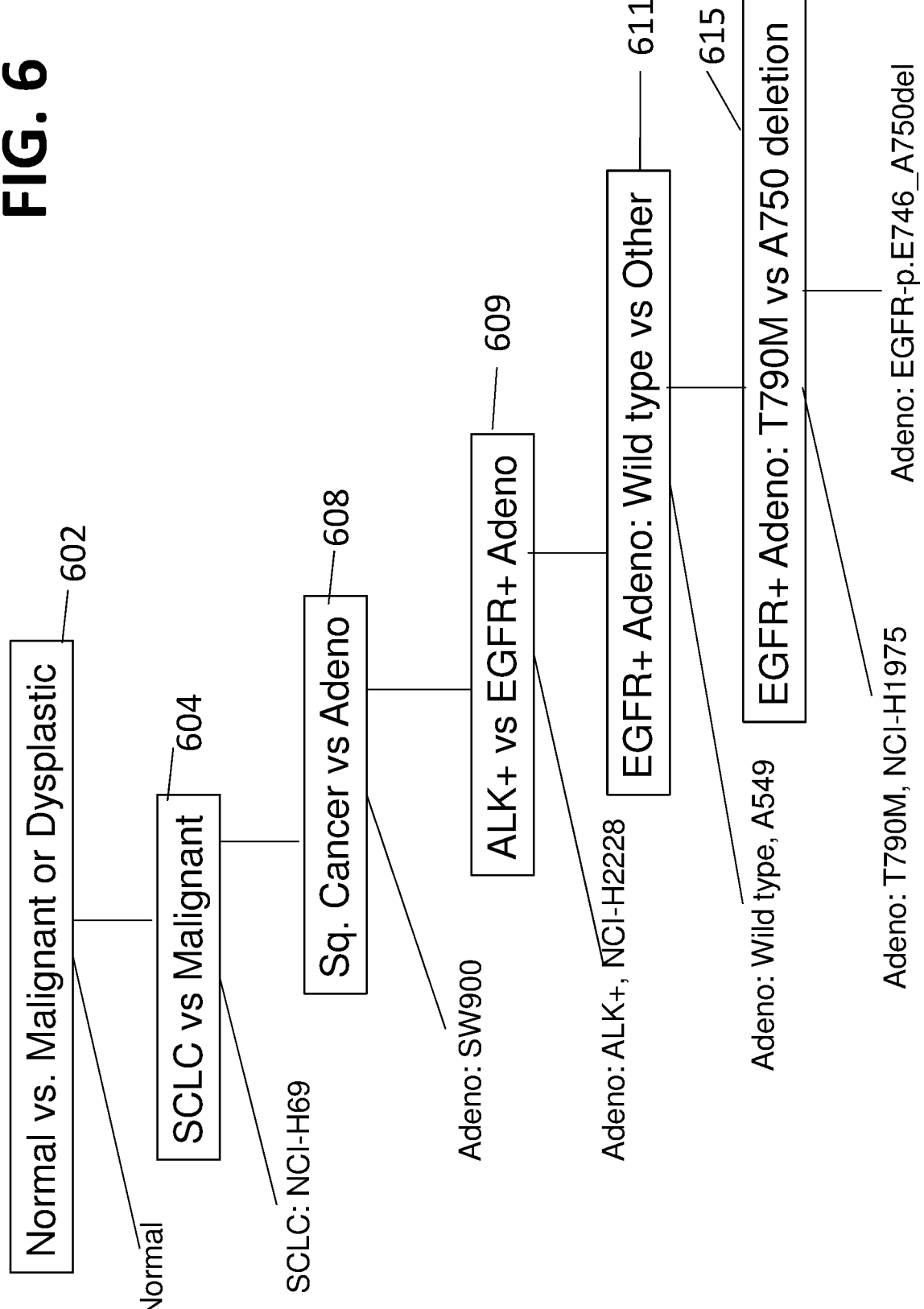
FIG. 6 schematically shows an example of a classification cascade to identify specific driver mutations associated with different lung cancers.

Referring now to FIG. 6, an example of a classification cascade for training classifiers adapted to identify specific mutations associated with different cancer types is shown. Training proceeded to produce a series of binary classifiers to isolate the desired cells including a first classifier 602, a second classifier 604, a third classifier 608, a fourth classifier 609, a fifth classifier 611, and a sixth classifier 615.

In one example, the first classifier 602 was trained for isolation of malignant cells from other normal cells. The first classifier 602 groups all the data from the malignant cell lines and assigns it to one class, for example, a set of malignant cells. The set of malignant cells plus the normal cells as negative control were used to train the first classifier to separate normal from malignant cells. This step is especially critical as malignant cells are rare in sputum. During training, the first classifier, functions by focusing a manual review conducted on only a very small portion of the cells in sputum. Since the manual review is a part of the process, it may be assumed that only abnormal cells that emerge from the process are truly malignant and may then be subtyped using the classifiers described below.

The second classifier 604 separates malignant subtypes. Any organ system has different types of tissue associated with it. For example, lung tissue is comprised of squamous epithelium and adenomatous tissue from the bronchi. Small cell lung cancer (SCLC) cells from the neuroendocrine glands are also sometime in evidence. Thus, a classifier is needed to isolate the specific cancer subtype in which the desired driver mutation occurs. This is done by first isolating small cell lung cancer from adenocarcinoma and squamous cancer and then isolating adenocarcinoma from squamous cancer. Further isolation of the desired mutation subtype within adenocarcinoma proceeds stepwise. The grouping of cell lines selected as a training set for this example is given in Table 1 below. Isolation of specific driver mutations is determined based on morphological factors in the third through sixth classifiers 608, 609, 611 and 615.

TABLE 1

| Classifier | Target Cell Type-Class1 | Cell Population-Class0 |
|---|---|---|
| Normal vs. Malignant or Dysplastic | Normal | NCI-H69, SW-900, A549, NCI-H1650, NCI-H1975, NCI-H2228 |
| SCLC vs Malignant | NCI-H69 | SW-900, A549, NCI-H1650, NCI-H1975, NCI-H2228 |
| Sq. Cancer vs Adeno | SW900 | A549, NCI-H1650, NCI-H1975, NCI-H2228 |
| ALK+ vs EGFR+ Adeno | NCI-H2228 | A549, NCI-H1650, NCI-H1975 |

TABLE 1-continued

| Classifier | Target Cell Type-Class1 | Cell Population-Class0 |
|---|---|---|
| EGFR+ Adeno: Wild type vs Other | A549 | NCI-H1650, NCI-H1975 |
| EGFR+ Adeno: T790M vs A750 deletion | NCI-H1975 | NCI-H1650 |

Still referring to FIG. 6, in one example, the stepwise isolation of mutation drivers begins with the first classifier 602 where a set of cells is isolated into normal and malignant or dysplastic classes. Any cells identified as malignant are further processed in the second classifier 604 which isolates SCLC: NCI-H69 type cells from other malignant cells which are passed to the third classifier 608. The third classifier 608 isolates Adeno: SW900 from other adenocarcinoma type cells and passes the other cells of the fourth classifier 609. The fourth classifier 609 isolates Adeno: ALK+, NCI-H2228 cell types from other remaining cell types and passes the remaining cell types to the fifth classifier 611. The fifth classifier 611 isolates Adeno: Wild type, A549 from EGFR+ Adeno cell types and passes the EGFR+ Adeno subtypes to the fifth classifier 615. The sixth classifier 615 isolates Adeno: T790M, NCI-H1975 from Adeno: EGFR-p.E746_A750del.

Those skilled in the art will recognize that this is only one example of an application of the invention and that other cell types and mutation drivers can be used to build and train classifiers according to the methods described herein. The invention is not limited in any way to this example. Classifier decisions are implemented by establishing decision boundary values for any measurable characteristic of a feature during classifier training. Thresholds may be selected or set according to instrument specifications, acceptable error rates, statistics, or other criteria according to accepted pattern recognition principles.

Experimental Results

Referring now to FIG. 7 where results of one experimental study are summarized in a table. A table 650 indicates the area under the ROC (aROC) 652 and the sensitivity 654 and specificity 656 for a target cell as classified by classifiers trained according to the training methods described above. Specificities relate to mis-identification of the malignant cells by a classifier that was intended to isolate a specific driver mutation. For example, the specificity for identification of cells from a small cell lung cancer (SCLC) tumor is 99.98%. The small number of cells that are called SCLC are in-fact from some of the other cell lines the table 650. Since only 0.02% of the malignant cells are misidentified the positive predictive value can be computed for identification of SCLC as PPV=TP/(TP+FP)=100*0.748/(0.748+0.002)=99.7.

The excellent discrimination between normal and abnormal cells in evidence for the LuCED® process combined with published evidence showing morphometric change for malignant cells that correlates to the genomic signature of the cell suggests that the genetic mutation responsible for driving the cancer process may be identified through purely morphological methods[52].

In this disclosure, an extension of the morphometric genomics concept used to detect cancer drivers into the domain of MMRD is provided. A 3D optical tomography system generates a morphometric classifier for non-invasively characterizing MMRD. LuCED® algorithms detect cancer with equal sensitivity irrespective of tumor histology, stage and size[46]. Therefore, a MMRD measure based on the Cell-CT would have the potential of non-invasively characterizing MMRD irrespective of histology, stage and size factors.

EXAMPLES

Figure 8A:
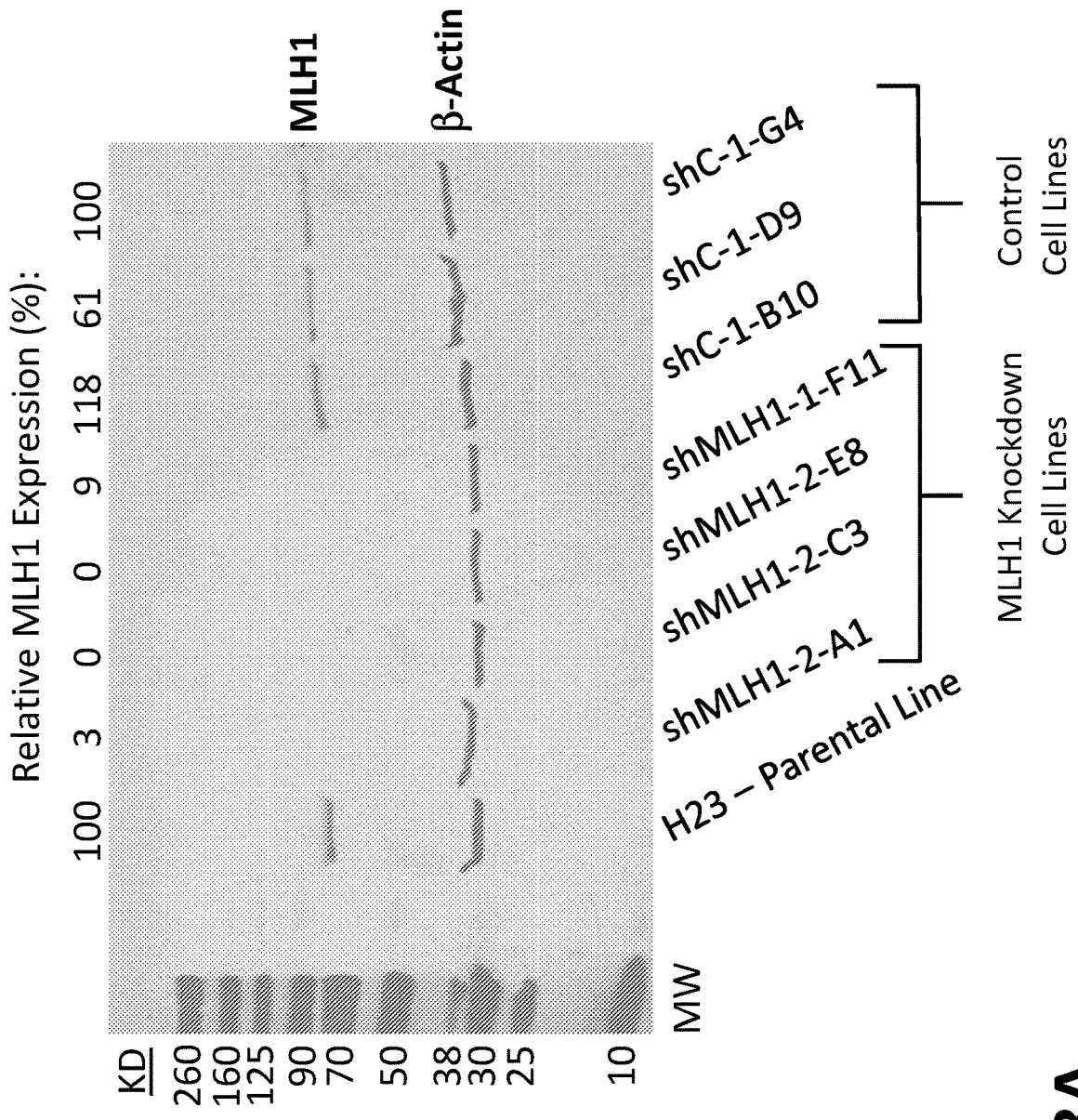
FIG. 8A and FIG. 8B, show Western blot analysis to quantify relative MLH1 expression from NCI-H23 and NCI-H1650 clones that are expressing either a control scrambled shRNA or shRNA targeting MLH1, respectively.
Figure 8B:
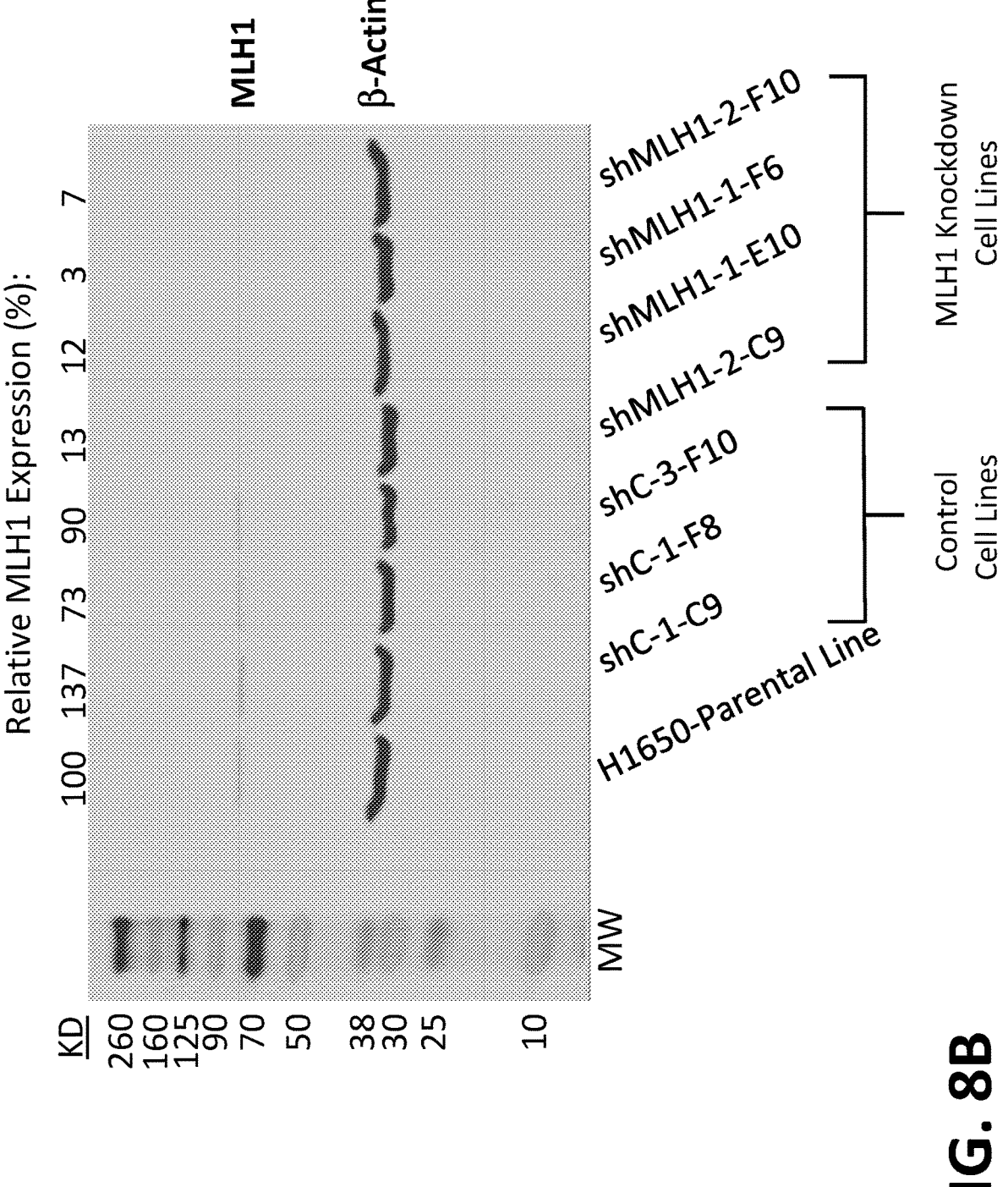

Data in Support of the Concepts Disclosed Herein are as Follows:

Starting with the NCI-H23 and NCI-H1650 human lung adenocarcinoma cell lines, which have functioning MMR activity and exhibit low TMB, clones were generated that exhibit MMRD via down-regulation of MLH1. Bailis et al.[53] (PLOS One. 2013 Oct. 29; 8(10):e78726) knocked-down expression of the MLH1 gene in NCI-H23 lung adenocarcinoma cells to generate isogenic lines for direct comparison of MMR-proficient and MMR Deficient cells. Bailis et al. reported that after several weeks in culture the MMR Deficient cells displayed genomic alterations such as microsatellite instability which is often correlated with high TMB. Taking advantage of these properties, NCI-H23 and NCI-H1650 cells were transduced with either MLH1 shRNA lentiviral particles (Santa Cruz Biotechnology, sc-35943-V) or scrambled shRNA lentiviral particles (Santa Cruz Biotechnology, sc-108080) and selected for integration using puromycin. Clones were derived from single puromycin-resistant cells by limited dilution into culture 96-well plates. Clones were first screened by immunohistochemistry using antibodies to MLH1 to select for control scrambled shRNA lines with wild-type expression and shMLH1 lines with silenced expression. As shown in FIG. 8A and FIG. 8B, clones were subsequently screened by Western blot analysis to quantify MLH1 expression. shMLH1 clones were obtained from both H23 and H1650 with reduced expression of MLH1 ranging from 0 to 13% of control levels.

Several harvests of each clone were fixed in an ethanol-based fixative and cells were analyzed on the VisionGate Cell-CT™ Platform. Over 1,000 cells from each harvest were used to measure 845 different 3D structural biomarkers for each cell. Using low and high MLH1 expression as a ground truth, a cell classifier was developed for each isogenic cell line and the area of ROC (aROC) was determined for each classifier. In general, this process involves defining a score that matches the ground truth for the cells in question. The classification process aims at producing a score that substantially matches the ground truth. The classification process was achieved using Adaptively boosted logistic regression[50]. This method uses principal components projection to define a projection axes that is then used through the logit function to produce a score ranging from 0 to 1. The algorithm is iterated with successive trials by weighting each observation by the differential between ground truth and the current score. This adaptive process converges on a solution that gradually adds a wider set of the cellular characteristics into the solution. Area under the ROC curve (aROC) is used to judge classifier efficacy. The aROC is calculated by computing the integral of the ROC curve, which represents the overall performance of a binary classifier output in terms of classification sensitivity and specificity. The term "sensitivity" refers to the ability of the classifier to correctly classify objects that possess a property (or a set of properties) that the classifier was trained to detect as "target" or positive object. Similarly, specificity represents the ability of the classifier to correctly classify objects as "non-target" or "negative", that do not possess the target property. Both sensitivity and specificity can range from 0 to 1, and it is desirable to have a classifier to perform with both parameters being as close to 1 as possible. Although a classifier produces for each object (cell, in our case) a continuous number (score, i.e. probability of the object to belong to the target class) as output, the output is further binarized by applying a threshold to the score that separates positive and negative classes. Once the classifier has been developed, the ROC curve can be generated by calculating the sensitivity and specificity values as a function of the threshold that is applied to separate the two object classes. The aROC value, which can range from 0 to 1, represents the percentage of true positive and true negative objects correctly classified by the classifier. In the present case, true positive objects are cells with MMRD (silenced MLH1 expression) and true negatives are cells with wild-type levels of MLH1. Thus, aROC>0.95 means that more than 95% of all cells with low or high MMRD will be correctly classified as such by the classifier.

MLH1-knockdown specific differences for both the H23 and H1650 line clones as compared to pooled shRNA clone data were observed. The aROC's for the four different H23 shMLH1 clones were 0.86, 0.81, 0.81, and 0.84, while those for three H1650 shMLH1 clones were 0.83, 0.80, and 0.90.

Thresholds can be established to use with the classifier score to create a binary output that correlates with the ground MMR with high accuracy. As described in the previous section, a classifier typically produces a numeric score representing the probability for a cell to belong to the target class. To separate the target from non-target cells, the scores are further made binary by applying a threshold to the scores distribution. Typically, the scores that lie above the threshold value are deemed as "positive" or target cells, whereas the objects with scores below the threshold are "negative" or non-target cells. As the value of the classifier threshold can be varied over the entire range of the scores distribution, the ultimate metric for choosing an appropriate numeric value is the highest possible accuracy of the classifier for correctly distinguishing (classifying) the cells. In our case, the threshold value will be determined such as to provide an accuracy of 0.95 or higher for separating cells with MMRD from those with normal MMR.

There are several methods that can be used to achieve this, some example methods include the following:

1. Adaptively boosted logistic regression[50] was used as noted above. This method uses principal components projection to define a projection axes that is then used through the logit function to produce a score ranging from 0 to 1. The algorithm is iterated with successive trials using by weighting each observation by the differential between ground truth and the current score. This adaptive process converges on a solution that gradually a wider set of the cellular characteristics into the solution.

2. Random Forest[51] method can also be employed alone or in combination with other methods. In this approach a classifier is produced using a non-parametric assumption for the feature distribution. One limitation of adaptive boosting is in assumptions for feature distributions that stand behind the principal components process. This is potentially problematic since the features may not strictly conform to the assumed distribution making the projection inaccurate. In this approach, a random vector is defined of random length. Discrimination is assessed, and the potential set of feature trees is pruned to optimize the discriminant.

As described in the previous section, a classifier typically produces a numeric score representing the probability for a cell to belong to the target class. To separate the target from non-target cells, the scores are further made binary by applying a threshold to the scores distribution. Typically, the scores that lie above the threshold value are deemed as "positive" or target cells, whereas the objects with scores below the threshold are "negative" or non-target cells. As the value of the classifier threshold can be varied over the entire range of the scores distribution, the ultimate metric for choosing an appropriate numeric value is the highest possible accuracy of the classifier for correctly distinguishing (classifying) the cells. In our case, the threshold value will be determined such as to provide an accuracy of 0.95 or higher for separating cells exhibiting high MMRD expression from cells exhibiting low MMRD expression.

Classifier Training—Inputs and Methods

Creation and optimization of cell detection classifiers is generally referred to as "classifier training," as the process aims to accurately diagnose cells according to a reference or ground truth. Using the classification methods described herein, cells can be classified into types including, but not limited to, normal, cancerous, and dysplastic. There are two main aspects to accuracy: first is specificity (normal cells being called normal by the classifier), and second is sensitivity (abnormal cells being called abnormal by the classifier). Algorithm training methods include Adaptively Boosted Logistic Regression and Random Forest. Those skilled in the art will be familiar with how to apply other classical training techniques for classifiers such as template methods, adaptive processing and the like.

The methods used to train the classifier ensure an extremely good outcome given the data used as input. Primarily, classifier accuracy is ensured when the inputs to the classifier training process accurately describe clinically relevant aspects of the cells and are robust to environmental factors that could influence optical tomography system results:

1. Three-dimensional cell images generated by the Cell-CTT optical tomography system have high resolution, allowing precise measurements of critical features that support correct classification.

2. Some features that are useful in classification emerge only in the 3D image. Consequently, the 3D feature set is not only more descriptive of the cell, but also richer making classification based on three-dimensional imaging more accurate versus 2D imaging.

3. Three-dimensional, image segmentation algorithms have been developed to isolate the whole cell from the background and the nucleus from the cell. The accuracy of these segmentation algorithms was verified by comparing the segmented trace with human derived cell or nuclear envelope traces.

4. Feature measurements describe various aspects of the cell, cell nucleus, cytoplasm and cell nucleoli. In one example of a test system, 594 features are computed for each 3D cell image that represent object shape, volume, distribution of chromatin, and other, subtler morphometric elements. Computation of these features has been verified to be independent of the orientation of the cell.

5. Diagnostic truth (the gold standard of pathology) for the classifier training is typically based on hierarchical cell diagnoses provided by two cytotechnologists and a cytopathologist.

Classifier Training—Statistical Considerations

Secondarily, in one test carried out by the inventors herein, accuracy of the classifier training process was ensured through a rigorous process that encompassed three aspects:

1. The database that was used to train the classifier was formulated to contain sufficient material to ensure that binomial 95% confidence intervals maintain variance of performance estimates within acceptable bounds.

2. Over-training is one potential pitfall of the training process where too much information could be included into the classifier so that the result could become over-specialized to the data used in the training. This situation generates an overly optimistic estimate for classifier performance. The risks of over-training can be mitigated through cross-validation which involves taking a portion of the training data and using it as testing data. Limits for the amount of information that can be used in the classifier are reached when performance estimates based on training data exceed the estimates from testing data 3. Finally, as further assurance against over-training, the classifier was tested on data from a second set of cells that were not a part of the training process.

Abnormal Cell Classifier Training Summary

The following considerations were used to define the parameters governing the training for the abnormal cell classifier:

1. Since abnormal cells samples are scarce, and non-diagnostic elements are plentiful the classifier must operate with high sensitivity and very high specificity. As described later in Table 1, high case detection sensitivity is maintained when the single cell classifier sensitivity is 75% and the specimen contains more than one abnormal cell.

2. To ensure workload is maintained within reasonable limits, the goal for specificity was set at 99%.

3. Intervals for the lower binomial 95% confidence bound [21] were to be maintained above 70% for sensitivity and 98.5% for specificity.

In the end, a high detection rate is desired for each positive case. Sensitivity of single cell detection translates to detection of the abnormal case as shown in Table 2.

TABLE 2

| Number of Abnormal Cells in the analysis | Case sensitivity based on 71% individual cell sensitivity (%) |
|---|---|
| 1 | 71.0 |
| 2 | 91.6 |
| 3 | 97.6 |

The implications of Table 2 are important for the lung cancer detection test. Results shown in this table indicate that if an abnormal cell is in the group analyzed by the lung cancer detection test, it will be confidently detected so that the case will be identified with high sensitivity. This leaves the question of abnormal cell presence in the lung cancer detection test analysis as the remaining factor determining the cancer detection rate.

Classifier Development and Features

Generally, features are computed to provide numerical representation of various aspects of the 3D tomogram. The computed features are used along with expert diagnosis of the objects to develop a classifier that can distinguish between object types. For example, a data set with M 3D tomograms computed for objects of a first type, type 1, and N 3D tomograms may be computed for objects of a second type, type 2, such as normal and abnormal cells. Here "M" and "N" represent the number of type 1 and type 2 values respectively. The data set is preferably generated by an optical tomography system. The optical tomography system provides 3D tomograms including 3D images of objects such as, for example, a cell. A cell typically includes other features such as a nucleus having organelles such as nucleoli. Object types may include differing types of cells, organelles, cells exhibiting selected disease states, probes, normal cells or other features of interest. A set of x 3D image features are computed based on 3D tomograms for all M+N objects. Next, a refined feature set of y 3D image features that best discriminate the object types is found, where "x" and "y" represent the number of 3D image features at each stage. The refined 3D image feature set of y 3D image features is used to build a classifier whose output correlates with the object type. In one example embodiment, a set of 3D tomograms is assembled, where the assembled set represent substantially all important markers that would be used by an expert to distinguish 3D biological object types. Having assembled a representative set of 3D tomograms, a 3D image feature set may be computed for each object that characterizes the important markers.

Features

Tomograms of biological objects, such as cells, exhibit a plurality of observable and measurable characteristics, some of which may be used as features for classification. Table 3 below provides a capsule summary of features, that is, important markers used to foster classification aims.

TABLE 3

FEATURES

| Feature Name | Brief Description |
|---|---|
| Volume | Number of connected voxels that comprise an object. |
| Surface Area | Number of voxels on the outer surface of a discrete object. |
| Shape features | Based on bounding box, surface area/volume ratio. |
| Location | Geometric center and center of mass of an object. |
| Voids | Based on a threshold T, number, volume, surface area, shape and location of inter-nuclear voids. |
| Invaginations | Based on a threshold T, count, size and location of nuclear invaginations. |
| Invagination Voids | Based on a threshold T, volume, surface area, shape, location of voids connected to invaginations. |
| Nucleoli | Based on a threshold T, volume, surface area, and shape, and location of objects likely to be nucleoli or chromatin condensations. |
| Nuclear texture features | The technique of a blur residue, using various sized structure elements, is used to separate various sized features within the nucleus. Overall 3D volume is then computed as are the number of discrete components, the volume histogram, average volume and variance, and shape histogram. |
| Distance metrics | Metrics describe spatial relationships between nucleoli, invaginations, voids, and the nuclear envelope. For example if three nucleoli are found the mean and variance, minimum and maximum inter-nucleoli distance may be found. Also the distance between the average coordinates for the cluster of the nucleoli and the center of mass for the entire object may be found. Similar calculations may be formed by substituting any of the above entities for the nucleoli and the nuclear center of mass. |

TABLE 3-continued

FEATURES

| Feature Name | Brief Description |
|---|---|
| FFT features | FFT of a 3D tomogram and FFT features characterize prominent and average FFT characteristics. |
| Histogram statistical features | Statistical features related to the 3D histogram of grey values for voxels such as kurtosis, the statistical moment of |
| 2D features | Two dimensional features include texture features such as blur residue and geometric features including perimeter and circularity of the object. |

By way of further explanation, in one useful example, voids occurring in 3D biological objects have now been found to be useful classification features based on measurement criteria including comparison with a calculated or selected threshold. Another characteristic related to voids may the include the number of voids in an object. Another characteristic related to voids includes volume of a void or number of voids. Yet another characteristic includes surface area of a void or number of voids. Shape and location of inter-nuclear voids may also be employed as a useful feature characteristic. Additionally, combinations of feature characteristics may also be used to build a classifier as described hereinabove.

Similarly, invaginations occurring in 3D biological objects have now been found to be useful classification features based on measurement criteria including comparison with a calculated or selected threshold. Another characteristic related to invaginations may include the number of invaginations in an object. Another characteristic related to invaginations includes volume of an invaginations or number of invaginations. Yet another characteristic includes size of an invagination or number of invaginations. Location of nuclear invaginations also comprises a useful feature characteristic. Additionally, combinations of feature characteristics may also be used to build a classifier as described hereinabove.

Invaginations occurring in 3D biological objects have now been found to be useful classification features based on measurement criteria including comparison with a calculated or selected threshold. Volume of invagination voids, surface area, shape, location of voids connected to invagi- nations and combinations of invagination features may also be advantageously used to build a classifier as described hereinabove.

Nucleoli occurring in 3D biological objects have now been found to be useful classification features based on measurement criteria including comparison with a calcu- lated or selected threshold. Volume, surface area, shape, location of objects likely to be nucleoli or chromatin con- densations and combinations of the aforesaid characteristics may also be advantageously used to build a classifier as described hereinabove. Nuclear texture features occurring in 3D biological objects have now been found to be useful classification features. Using various sized structure ele- ments, the technique of blur residue is used to separate various sized features within the nucleus. Blur residue techniques typically require blurring an image using a filter and measuring the resultant blur residue by applying mark- ing operations. Overall 3D volume is then computed as are the number of discrete components, the volume histogram, average volume and variance, and shape histogram.

Distance metrics that describe spatial relationships between nucleoli, invaginations, voids, and the nuclear envelope have now been found to be useful classification features. For example, if three nucleoli are found the mean and variance, minimum and maximum inter-nucleoli distance may be found. Also, the distance between the average coordinates for the cluster of the nucleoli and the center of mass for the entire object may be found. Similar calculations may be formed by substituting any of the above entities for the nucleoli and the nuclear center of mass.

Fast Fourier Transform (FFT) features now have also been found to be useful classification features. FFT features are formed by a Fast Fourier Transform of a 3D tomogram. The FFT features characterize prominent and average characteristics of the FFT classification.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

The disclosures of the following publications are incorporated herein by reference.

1. Reddy K., Feinberg A. Higher order chromatin organization in cancer. Seminars in Cancer Biol. 2013:23: 109-115.
2. Mattout A., Cabianca D., Gasser S., Chromatin states and nuclear organization in development—a view from the nuclear lamina. Genome Biol., 2015; 16:174.
3. Zink, D., Fischer, A., Nickerson J. Nuclear structure in cancer cells. Nat. rev. Cancer. 2004:4:677-687.
4. Polak, P., Karlić, R., Koren, A., Thurman, R., Sandstrom, R., Lawrence, M., Reynolds, A. et al., Cell-of-origin chromatin organization shapes the mutational landscape of cancer. Nature, 2015; 518:360-364.
5. Schuster-Boeckler B., Lehner, B. Chromatin organization is a major influence on regional mutation rates in human cancer cells. Nature, 2012; 488:504-507.
6. Pardoll D M. The blockade of immune checkpoints in cancer immunotherapy. Nat Rev Cancer. 2012 Mar. 22; 12(4): 252-64.
7. Robert C, Long G V, Brady B, Dutriaux C, Maio M, Mortier L, et al. Nivolumab in previously untreated melanoma without BRAF mutation. N Engl J Med 2015; 372:320-30.
8. Weber J S, D'Angelo S P, Minor D, Hodi F S, Gutzmer R, Neyns B, et al. Nivolumab versus chemotherapy in patients with advanced melanoma who progressed after anti-CTLA-4 treatment (CheckMate 037): a randomised, controlled, open-label, phase 3 trial. Lancet Oncol 2015; 16:375-84.
9. Borghaei H, Paz-Ares L, Horn L, Spigel D R, Steins M, Ready N E, et al. Nivolumab versus docetaxel in advanced nonsquamous non-small-cell lung cancer. N Engl J Med 2015; 373:1627-39.
10. Gangadhar, Tara C., Vonderheide, Robert H. Mitigating the toxic effects of anticancer immunotherapy, Nat. Rev. Clin. Oncol. 2014; 11(2): 91-99.
11. Byun, D., Wolchok, J., Rosenberg, L. M., Girotra, M., Cancer immunotherapy—immune checkpoint blockade and associated endocrinopathies. 2017; 13:195-207.
12. Abdel-Wahab, N., Alshawa, A., Suarez-Almazor, M. Adverse effects in cancer immunotherapy. Adv. Exp. Med. Biol., 2017; 995:155-174.
13. Hodi F S, O'Day S J, McDermott D F, Weber R W, Sosman J A, Haanen J B, et al. Improved survival with ipilimumab in patients with metastatic melanoma. N Engl J Med 2010; 363:711-23
14. Motzer R J, Escudier B, McDermott D F, George S, Hammers H J, Srinivas S, et al. Nivolumab versus everolimus in advanced renal-cell carcinoma. N Engl J Med 2015; 373:1803-13
15. Voong K R, Feliciano J, Becker D, Levy B. Beyond PD-L1 testing-emerging biomarkers for immunotherapy in non-small cell lung cancer. Ann Transl Med. 2017 September; 5(18): 376.
16. Danilova L, Wang H, Sunshine J, Kaunitz G J, Cottrell T R, Xu H, Esandrio J, Anders R A, Cope L, Pardoll D M, Drake CG1, Taube J M. Association of PD-1/PD-L axis expression with cytolytic activity, mutational load, and prognosis in melanoma and other solid tumors. Proc Natl Acad Sci USA. 2016 Nov. 29; 113(48): E7769-E7777.
17. Kefford R., Ribas A., Hamid O., et al. Clinical efficacy and correlation with tumor PD-L1 expression in patients with melanoma treated with the anti-PD-1 monoclonal antibody MK-3475. Journal of Clinical Oncology. 2014; 32 ([supplement: abstr 3005])
18. Carbognin L., Pilotto S., Milella M., et al. Differential activity of nivolumab, pembrolizumab and MPDL3280A according to the tumor expression of programmed death-ligand-1 (PD-L1): sensitivity analysis of trials in melanoma, lung and genitourinary cancers. PLOS ONE. 2015; 10(6)
19. Muro K., Bang Y., Shankaran V., et al. Relationship between PD-L1 expression and clinical outcomes in patients (Pts) with advanced gastric cancer treated with the anti-PD-1 monoclonal antibody pembrolizumab (Pembro; MK-3475) in KEYNOTE-012. Journal of Clinical Oncology. 2015; 33 ([supplement; abstr 3]): 3-3.
20. Madore J., Vilain R. E., Menzies A. M., et al. PD-L1 expression in melanoma shows marked heterogeneity within and between patients: Implications for anti-PD-1/PD-L1 clinical trials. Pigment Cell and Melanoma Research. 2015; 28(3): 245-253.
21. Mitchell P., Murone C., Asadi K., et al. PD-L1 expression in NSCLC: analysis of a large early stage cohort; and concordance of expression in primary, node and metastasis. Journal of Thoracic Oncology. 2015; 10 ([supplement; S199 abstr]
22. Le D T, Durham J N, Smith K N, Wang H, Bartlett B R, Aulakh L K, Lu S, Kemberling H, Wilt C, Luber B S, Wong F, Azad N S, Rucki A A, Laheru D, Donehower R, Zaheer A, Fisher G A, Crocenzi T S, Lee J J, Greten T F, Duffy A G, Ciombor K K, Eyring A D, Lam B H, Joe A, Kang S P, Holdhoff M, Danilova L, Cope L, Meyer C, Zhou S, Goldberg R M, Armstrong D K, Bever K M, Fader A N, Taube J, Housseau F, Spetzler D, Xiao N, Pardoll D M, Papadopoulos N, Kinzler K W, Eshleman J R, Vogelstein B, Anders R A, Diaz L A Jr. Mismatch repair deficiency predicts response of solid tumors to PD-1 blockade. Science. 2017 Jul. 28; 357(6349): 409-413.
23. Viale G, Trapani D, Curigliano G. Mismatch Repair Deficiency as a Predictive Biomarker for Immunotherapy Efficacy. Biomed Res Int. 2017; 2017:4719194.
24. Boussiotis V. A. Somatic mutations and immunotherapy outcome with CTLA-4 blockade in melanoma. Journal of Medicine. 2014; 371(23): 2230-2232.

25. Goodman A M, Kato S, Bazhenova L, Patel S P, Frampton G M, Miller V, Stephens P J, Daniels G A, Kurzrock R. Tumor Mutational Burden as an Independent Predictor of Response to Immunotherapy in Diverse Cancers. Mol Cancer Ther. 2017 November; 16(11): 2598-2608.

26. Rizvi N. A., Hellmann M. D., Snyder A. Mutational landscape determines sensitivity to PD-1 blockade in non-small cell lung cancer. Science. 2015; 348(6230): 124-128.

27. Carbone D P, Reck M, Paz-Ares L, Creelan B, Horn L, Steins M, Felip E, van den Heuvel M M, Ciuleanu T E, Badin F, Ready N, Hiltermann T J N, Nair S, Juergens R, Peters S, Minenza E, Wrangle J M, Rodriguez-Abreu D, Borghaei H, Blumenschein G R Jr, Villaruz L C, Havel L, Krejci J, Corral Jaime J, Chang H, Geese W J, Bhagavatheeswaran P, Chen A C, Socinski M A; CheckMate 026 Investigators. First-Line Nivolumab in Stage IV or Recurrent Non-Small-Cell Lung Cancer. N Engl J Med. 2017 Jun. 22; 376(25): 2415-2426.

28. Davis A A, Chae Y K* and Giles F J. Is Circulating Tumor DNA (Ctdna) Use Ready For Prime Time? Applications and Challenges of Ctdna in the Era of Precision Oncology. Chemo Open Access 2017, 6:2

29. Chae Y K, Davis A A, Jain S, Santa-Maria C, Flaum L, Beaubier N, Platanias L C, Gradishar W, Giles F J, Cristofanilli M. Concordance of Genomic Alterations by Next-Generation Sequencing in Tumor Tissue versus Circulating Tumor DNA in Breast Cancer. Mol Cancer Ther. 2017 July; 16(7): 1412-1420.

30. Kim H, Jen J, Vogelstein B, Hamilton S R. Clinical and pathological characteristics of sporadic colorectal carcinomas with DNA replication errors in microsatellite sequences. Am J Pathol. 1994 July; 145(1): 148-56.

31. Ward R, Meagher A, Tomlinson I, O'Connor T, Norrie M, Wu R, Hawkins N. Microsatellite instability and the clinicopathological features of sporadic colorectal cancer. Gut 2001 June; 48(6): 821-9.

32. Greenson J K, Bonner J D, Ben-Yzhak O, Cohen H I, Miselevich I, Resnick M B, Trougouboff P, Tomsho L D, Kim E, Low M, Almog R, Rennert G, Gruber S B. Phenotype of microsatellite unstable colorectal carcinomas: Well-differentiated and focally mucinous tumors and the absence of dirty necrosis correlate with microsatellite instability. Am J Surg Pathol. 2003 May; 27(5): 563-70.

33. Alexander J, Watanabe T, Wu T T, Rashid A, Li S, Hamilton S R. Histopathological identification of colon cancer with microsatellite instability. Am J Pathol. 2001 February; 158(2): 527-35.

34. David Gisselsson, Jonas Bjork, Mattias Höglund, Fredrik Mertens, Paola Dal Cin, Måns Åkerman, and Nils Mandahl. Abnormal Nuclear Shape in Solid Tumors Reflects Mitotic Instability. Am J Pathol. 2001 January; 158(1): 199-206.

35. Bai H, Madabushi A, Guan X, Lu A L. Interaction between human mismatch repair recognition proteins and checkpoint sensor Rad9-Rad1-Hus1. DNA Repair (Amst). 2010 May 4; 9(5): 478-87.

36. Debes J D, Sebo T J, Heemers H V, Kipp B R, Haugen D L, Lohse C M, Tindall D J. p300 modulates nuclear morphology in prostate cancer. Cancer Res. 2005 Feb. 1; 65(3): 708-12.

37. Ionov Y, Matsui S, Cowell J K. A role for p300/CREB binding protein genes in promoting cancer progression in colon cancer cell lines with microsatellite instability. Proc Natl Acad Sci USA. 2004 Feb. 3; 101(5): 1273-8.

38. Koshiishi N, Chong J M, Fukasawa T, Ikeno R, Hayashi Y, Funata N, Nagai H, Miyaki M, Matsumoto Y, Fukayama M. p300 gene alterations in intestinal and diffuse types of gastric carcinoma. Gastric Cancer. 2004; 7(2): 85-90.

39. Pihan G A, Purohit A, Wallace J, Malhotra R, Liotta L, Doxsey S J. Centrosome defects can account for cellular and genetic changes that characterize prostate cancer progression. Cancer Res. 2001 Mar. 1; 61(5): 2212-9.

40. Robinson H M, Black E J, Brown R, Gillespie D A. DNA mismatch repair and Chk1-dependent centrosome amplification in response to DNA alkylation damage. Cell Cycle. 2007 Apr. 15; 6(8): 982-92.

41. Bornens M. Cell polarity: intrinsic or externally imposed? New Biol., 3:627-636, 1991.

42. Rizzolo L. J., Joshi H. C. Apical orientation of the microtubule organizing center and associated γ-tubulin during the polarization of the retinal pigment epithelium in vivo. Dev. Biol., 157:147-156, 1993.

43. Meads T., Schroer T. A. Polarity and nucleation of microtubules in polarized epithelial cells. Cell Motil. Cytoskeleton, 32:273-288, 1995.

44. Whitehead C. M., Salisbury J. L. Regulation and regulatory activities of centrosomes. J. Cell. Biochem., 32-33 (Suppl.): 192-199, 1999.

45. Meyer M., Hayenga J W, Neumann T, Katdare R, Presley C, Steinhauer D E, Bell T M, Lancaster C A, Nelson A C. The Cell-CT 3-Dimensional Imaging Technology Platform Enables the Detection of Lung Cancer Using the LuCED Sputum Test. Cancer Cytopathology, 123(9): 512-523, 2015

46. Wilbur D., Meyer M G, Presley C, Aye R W, Zarogoulidis P, Johnson D W, Peled N, Nelson A C. Automated 3-Dimensional Morphologic Analysis of Sputum Specimens for Lung Cancer Detection: Performance Characteristics Support Use in Lung Cancer Screening. Cancer Cytopathology, 123(9): 548-556, 2015

47. Fauver M, Seibel E. Rahn J. Three-dimensional imaging of single isolated cell nuclei using optical projection tomography. Optics Express, 13:4210-4223, 2005.

48. Deans S. The Radon Transform and Some of Its Applications, New York: Dover Publishers: 2007

49. Rawski [Accessed Mar. 19, 2015]; Maximum intensity projection (MIP) Retrieved from Radiopaedia.org URL http://radiopaedia.org/articles/maximum-intensity-projection-mip.

50. Schapire R, Freund Y. Boosting, Foundations and Algorithms, Cambridge: MIT Press, 2012

51. Breiman L. Random Forests. Machine Learning, 45:5-32, 2001

52. Nelson A., M. Meyer, D. Sussman, R. Katdare, C. Presley, F. Lakers, C. Hamilton, D. Wilbur, R. Mastrangelo, M. Doherty Morphometric Genotyping Identifies Lung Cancer Cells Harboring Target Mutations; Cell-CT Platform Detects Gene Abnormalities, Journal of Thoracic Oncology, 12(11) (Supplement 2): S2278-S2279, 2017

53. Bailis J M, Gordon M L, Gurgel J L, Komor A C, Barton J K, Kirsch I R. An inducible, isogenic cancer cell line system for targeting the state of mismatch repair deficiency. PLOS One. 8: e78726, 2013

What is claimed is:

1. A method for developing at least one more morphometric classifier to identify cells exhibiting Mismatch Repair Deficiency (MMRD), the method comprising:

actuating a mirror to sweep a plane of focus through transduced cells, wherein projection images are integrated by the camera to create a pseudoprojection from each single perspective;

deriving selected clones from the transduced cells, using a software-executed process that interfaces with opto-mechanical devices;

using a 3D optical tomography system for MLH1 expression to identify a subset of MLH1 expression clones by viewing the projection images of the selected clones from multiple angular positions;

using immunohistochemistry antibodies to select the subset of MLH1 expression clones to identify those with MLH1 expression levels reduced in comparison to a parental cell line to identify a second subset of the selected clones;

expanding the second subset of the selected clones in culture;

harvesting the second subset of the selected clones;

using the selected clones and 3D cell classifications to generate a morphometric classifier, via the 3D optical tomography system, for non-invasively characterizing MMRD;

using a classification cascade to train the morphometric classifier to identify specific mutations associated with different cancer types, wherein the training produces a series of binary classifiers to isolate malignant cells from normal cells;

using the morphometric classifier trained on the selected clones to detect cancer drivers in the MMRD; and treating a patient with an immune checkpoint inhibitor agent, in response to detecting cancer drivers in the MMRD, wherein the morphometric classifier detects cancer with equal sensitivity irrespective of tumor histology, stage, and size.

2. The method of claim 1 wherein the selected clones are selected from the group consisting of a cultured cell line, parental NCI-H23 and NCI-H1650 human lung adenocarcinoma cell lines and combinations thereof.

3. The method of claim 1 wherein the step of analyzing generates a plurality of morphometric biosignatures.

4. The method of claim 3 further comprising using cells exhibiting wild type endogenous MMRD expression as a ground truth for developing a cell classifier for at least one cell in an isogenic cell line.

* * * * *